United States Patent [19]

Davies

[11] Patent Number: 4,847,242

[45] Date of Patent: Jul. 11, 1989

[54] 11-ETHER DERIVATIVES OF ERYTHROMYCINS

[75] Inventor: John S. Davies, Reigate, England

[73] Assignee: Beecham Group p.l.c., England

[21] Appl. No.: 838,297

[22] Filed: Mar. 10, 1986

[30] Foreign Application Priority Data

Mar. 12, 1985 [GB] United Kingdom ............... 8506381
Mar. 23, 1985 [GB] United Kingdom ............... 8507626
Jan. 10, 1986 [GB] United Kingdom ............... 8600553

[51] Int. Cl.[4] ................. A61K 31/70; C07H 17/08
[52] U.S. Cl. .................................. 514/29; 536/7.2; 536/7.4
[58] Field of Search ................ 536/7.2, 7.4; 514/29

[56] References Cited

U.S. PATENT DOCUMENTS 3,780,019 12/1973 Wildsmith ........................... 536/7.4
3,884,904 5/1975 Jones et al. ........................ 536/7.2
4,016,263 4/1977 Wetzel et al. ..................... 536/7.4

FOREIGN PATENT DOCUMENTS 0080818 6/1983 European Pat. Off. ............ 536/7.2

OTHER PUBLICATIONS

March, *Advanced Organic Chemistry:* Reactions, Mechanisms, and Structure, 1968, p. 316.

*Primary Examiner*—Ronald W. Griffin
*Assistant Examiner*—Elli Peselev
*Attorney, Agent, or Firm*—Jacobs & Jacobs

[57] ABSTRACT

11-ether derivatives of erythromycin, and corresponding 9-(optionally substituted)-amino, 9-imino, and 9-(optionally substituted)-oxime derivatives are novel antibacterially active compounds, and can be prepared by alkylation of the 11-hydroxy group under mild conditions.

36 Claims, No Drawings

11-ETHER DERIVATIVES OF ERYTHROMYCINS

The present invention relates to novel chemical compounds, their preparation and their use, and in particular to a novel class of erythromycin derivatives. These compounds have antibacterial properties, in particular against Gram-positive bacteria but also against some Gram-negative bacteria, and they are therefore of use in the treatment of bacterial infections in humans and animals caused by a wide range of organisms.

Erythromycin was first described in U.S. Pat. No. 2,653,899 (R. L. Bunch et al; Eli Lilly). The structure of erythromycins can be represented as follows:

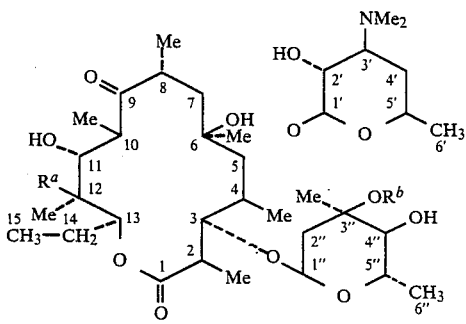

in which
$R^a$ denotes hydrogen or hydroxy and
$R^b$ denotes hydrogen or methyl.

The basic erythromycin structure comprises:
(i) a 14-membered lactone ring, referred to as the erythonolide ring, numbered with unprimed digits as shown in the above formula,
(ii) a first sugar ring, known as the desosamine ring, numbered with single-primed digits, and
(iii) a second sugar ring, known as the cladinose ring, numbered with double-primed digits.

The erythronolide ring can exist in two forms:
erythronolide A (n which $R^a$=OH)
erythronolide B (in which $R^a$=H).

The four main naturally occurring erythromycins are as follows:

| Erythromycin | $R^a$ | $R^b$ |
|---|---|---|
| A | OH | CH$_3$ |
| B | H | CH$_3$ |
| C | OH | H |
| D | H | H | of which erythromycin A is by far the most important.

Erythromycins, and in particular erythromycin A, are antibiotics widely employed clinically in the treatment of infections caused by Gram-positive and some Gram-negative bacteria. A major drawback of erythromycins is their poor acid stability, resulting in poor and erratic oral absorption.

Numerous attempts have been made to modify erythromycin to produce derivatives having improved acid stability without loss of the antibacterial activity.

(9S)-9-Dihydroerythromycin A (which carries a 9-hydroxy group in place of the 9-keto group) has been described, but has poor antibacterial activity (P. F. Wiley et al, *J. Amer. Chem. Soc.*, 1955, 77, 3676–3677; M. V. Sigal et al, ibid, 1956, 78, 388–395; and T. Glabski et al, *Roczniki Chem.*, 1976, 50, 1281). Erythromycylamine and erythromycin oxime (in which the 9-keto group is replaced, respectively, by an amino or oxime group), as well as various N-substituted derivatives of erythromycylamine have also been described (GB No. 1 100 504 (Pliva Pharmaceutical); E. H. Massey et al, *Tetrahedron Letters,* 1970, No. 2, 157–160; and G. H. Timms et al, ibid, 1971, No. 2, 195–198), as have various erythromycin oxime ethers (U.S. Pat. No. 3,681,326 (A. M. Von Esch; Abbott Laboratories); U.S. Pat. Nos. 3,869,445 and 4,063,014 (both R. Hallas et al; Abbott Laboratories); and U.S. Pat. No. 4,349,545 (S. Gouin d'Ambrieres; Roussel-Uclaf); and *Antimicrobial agents and chemotherapy,* 1974, 6, 479).

Certain aldehyde-erythromycylamine condensation products with a 9-N,6-O- or 9-N,11-O-cyclic substituent have previously been disclosed (U.S. Pat. No. 4,048,306 (R. Maier et al; Boehringer Ingelheim GmbH)).

4''-Deoxy-11-O-methylthiomethyl-4''-oxo-erythromycin B and its conversion to (i) 4''-deoxy-9,11O-(optionally substituted)methylene-4''-oxo-erythromycin B 6,9-hemiacetal and the corresponding 4''-epi-hydroxy, 2',4''-O-diacetyl-4''-epi, and 4'-O-acetyl-4''-epi derivatives, and (ii) 4''-deoxy-4''-oxo-, 4''-O-acetyl-4''-epi-, and 4''-epi-erythromycin B; as well as 4''-O-formyl-11-O-methylthiomethyl-erythromycin B and its conversion to 11-O-methylthiomethyl-erythromycin B, 9,11-O-meth-ylene-erythromycin B 6,9-hemiacetal, 11-O-methyl-erythromycin B and 11-O-n-butylerythromycin B; and also 4''-deoxy-4''-oxoerythromycin A are described in U.S. Pat. Nos. 3,842,069, 3,884,903 and 3,884,904 (all P. H. Jones et al; Abbott Laboratories).

4''-Deoxy-4''-amino-erythromycin A, 4''-deoxy-4''-amino-erythromycin A 6, 9-hemiketal, and 4''-deoxy -4''-oxo-erythromycin A 6,9-hemiketal, as well as corresponding 11-O-acetyl and 11,12-cyclic carbonate derivatives, and also 4''-deoxy-4''-amino-erythromycin B and 4''-deoxy-4''-oxo-erythromycin A 4''-O-oxime or 4''-O-acetyloxime, are described in U.S. Pat. No. 4,150,220 (F. C. Sciavolino; Pfizer).

An 11,12-cyclic carbonate of 9-dihydroerythromycin has also been described in T. Glabski et al; *Roczniki Chem.,* 1976, 50, 1281 and 9-dihydro-11,12-O-isopropylidene-erythromycin A and the corresponding 4''-epi compound have been described in U.S. Pat. No. 4,382,086 (F. C. Sciavolino et al; Pfizer).

6-O-Methyl-, 6,11-di-O-methyl-, 11-O-methyl- and 11-O-ethyl-erythromycin A, and also 6-O-methyl-6,4''-di-O-methyl-, and 6,11,4''-tri-O-methyl-erythromycin B are described in EP No. 0,041,355 A1, EP No. 0,080,818 A1 and EP No. 0,080,819 A1 (all Taisho Pharmaceutical). 6-O-methyl-erythromycin A derivatives and their preparation are also described in EP No. 0,158,467 A2 (Taisho; priority 06 Apr. 1984, filed 22 Mar. 1985 (subsequent to the first priority date of the present application), published Oct. 16, 1985).

The erythromycin derivatives according to the present invention in general possess improved bioavailability as compared with erythromycin A while retaining good antibacterial activity.

The present invention provides antibacterially active 11-ether derivatives of erythromycin, and corresponding 9-(optionally substituted)amino, 9-imino, and 9-(optionally substituted)oxime compounds.

In particular, the present invention provides a compound of the general formula I or a pharmaceutically acceptable ester or acid addition salt thereof:

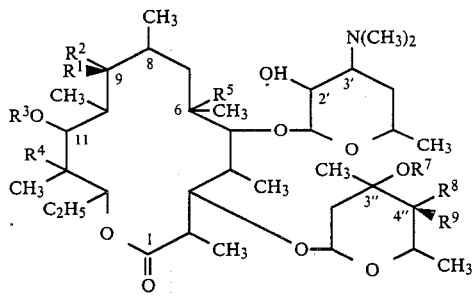

wherein
one of $R^1$ and $R^2$ denotes hydrogen and the other of $R^1$ and $R^2$ denotes an amino group or a substituted amino group, or $R^1$ and $R^2$ together denote an oxo group, an oxime group, a substituted oxime group, or an imino group, and $R^5$ denotes a hydroxy group or an alkoxy group; or one of $R^1$ and $R^2$ denotes a hydroxy group, or an amino group, and the other of $R^1$ and $R^2$ together with $R^5$ denotes an ether oxygen atom, —O—, $R^3$ denotes a group of the formula II:

in which
Q denotes one of the following groups:

 IIIA

 IIIB

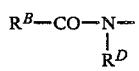 IIIC

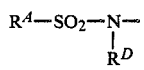 IIID $R^A$ denotes an unsubstituted or substituted hydrocarbon group, $R^B$ denotes a hydrogen atom or an unsubstituted or substituted hydrocarbon or hydrocarbon-oxy group, each of $R^C$ and $R^D$, which may be identical or different, denotes a hydrogen atom or an unsubstituted or substituted hydrocarbon group, or any two of $R^A$, $R^B$, $R^C$ and $R^D$ together denote a divalent, unsubstituted or substituted, organic group forming a 4- to 7-membered heterocyclic ring together with the intervening atoms of the molecule;

$R^4$ denotes hydrogen or hydroxy;

$R^7$ denotes hydrogen or methyl;

one of $R^8$ and $R^9$ denotes hydrogen, hydroxy, alkoxy, alkanoyloxy, amino, substituted amino, or a group of the formula $R^{12}$—SO$_2$—O—, and the other of $R^8$ and $R^9$ denotes hydrogen, or $R^8$ and $R^9$ together denote an oxo group, an oxime group, or a substituted oxime group; and $R^{12}$ denotes an organic group.

The term 'hydrocarbon' as used herein includes groups having up to 18 carbon atoms, suitably up to 10 carbon atoms, conveniently up to 6 carbon atoms. Suitable hydrocarbon groups include $(C_{1-6})$alkyl, $(C_{2-6})$alkenyl, $(C_{2-6})$alkynyl, $(C_{3-7})$cycloalkyl, aryl, $(C_{3-7})$cycloalkyl$(C_{1-6})$alkyl, aryl$(C_{1-6})$alkyl, $(C_{1-6})$alkyl$(C_{3-7})$cycloalkyl, and $(C_{1-6})$alkylaryl.

Examples of suitable optional substituents for the above-mentioned hydrocarbon groups include heterocyclyl, amino, $(C_{1-6})$alkanoylamino, (mono, di, or tri)-$(C_{1-6})$alkylamino, hydroxy, $(C_{1-6})$alkoxy, mercapto, $(C_{1-6})$alkylthio, heterocyclylthio, arylthio, sulphamoyl, carbamoyl, amidino, guanidino, nitro, halogen (for example chloro, bromo, fluoro), carboxy and salts and esters thereof, acyl and acyloxy groups.

Any alkyl group or moiety referred to herein may be straight or branched, unsubstituted or substituted, and may contain, for example, up to 12 carbon atoms, suitably up to 6 carbon atoms. In particular, the alkyl group or moiety may be an unsubstituted or substituted methyl, ethyl, n-propyl, iso-propyl, n-butyl, sec-butyl, isobutyl or tert-butyl group. Examples of suitable optional substitutents for any such alkyl group or moiety include the above-listed substitutents for hydrocarbon groups, and also the above-listed non-alkyl hydrocarbon groups, for example $(C_{2-6})$alkenyl and aryl groups.

The term 'aryl' as used herein includes phenyl and naphthyl, which may be unsubstituted or substituted by up to five, preferably up to three, groups selected from the above-listed substituents for hydrocarbon groups, and the above-listed hydrocarbon groups, including, for example, substituents selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkanoyloxy, and $(C_{1-6})$alkyanoyl groups.

The term 'acyl' as used herein includes unsubstituted and substituted hydrocarbon-carbonyl and hydrocarbonyoxy-carbonyl groups, including, for example, unsubstituted and substituted alkanoyl, cycloalkylcarbonyl, arylcarbonyl, alkoxycarbonyl, aryloxycarbonyl, and heterocyclylcarbonyl groups. The term 'acyloxy' is used analogously.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo $(C_{1-6})$alkyl, hydroxy, amino, carboxy, carboxy salts, carboxy esters, $(C_{1-6})$alkoxycarbonyl, $(C_{1-6})$alkoxycarbonyl $(C_{1-6})$alkyl, aryl, and oxo groups. Each heterocyclic ring suitably has from 4 to 7, preferably 5 or 6, ring atoms. A fused heterocyclic ring system may include carbocyclic rings and need include only one heterocyclic ring.

The term 'heteroaryl' as used herein means an aromatic heterocyclic ring or ring system, suitably having 5 or 6 ring atoms in each ring.

In one group of compounds of the general formula I, $R^1$ and $R^2$ together denote an oxo group, as in naturally occurring erythromycins, although in some cases such compounds may exist as a 6,9-hemiketal tautomer. In a second group of compounds of the general formula I, $R^1$ and $R^2$ together denote an oxime group (also referred to as a hydroxyimino group, =NOH) or a substituted oxime group (for example, an oxime ether group or an acyl-oxime group). Such compounds may be referred to as erythromycin oxime derivatives. In a third group of compounds of the general formula I, $R^1$ and $R^2$ together denote an imino group; such compounds may be referred to as erythromycin imines, and may in some cases exist as a 6,9-carbinolamine ether tautomer. In a fourth group of compounds of the general formula I, one of $R^1$ and $R^2$ denotes an amino group or a substituted amino group, and the other of $R^1$ and $R^2$ denotes a hydrogen atom; such compounds may be referred to as erythromycylamines.

The compounds in which $R^1$ and $R^2$ together denote an oxo group and $R^5$ denotes a hydroxy group may exist in the alternative tautomeric for in which one of $R^1$ and $R^2$ denotes a hydroxy group and the other of $R^1$ and $R^2$ together with $R^5$ denotes an ether oxygen atom. Such tautomeric forms may exist in equilibrium.

When $R^1$ and $R^2$ together denote an oxo group, suitably $R^5$ denotes an alkoxy group. Such compounds have the advantage of improved acid stability as compared with the 6-hydroxy-9-oxo compounds.

Advantageously, $R^1$ and $R^2$ together denote an oxime or substituted oxime group. Such compounds also generally have the advantage of improved acid stability as compared with the 6-hydroxy-9-oxo compounds. In the case of the erythromycin oxime and substituted oxime derivatives according to the invention, $R^1$ and $R^2$ may together denote a group of the formula IV:

$$=N\text{---}O\text{---}R^{13} \qquad \text{IV}$$

in which $R^{13}$ denotes hydrogen or an unsubstituted or substituted hydrocarbon group or an acyl group. Examples of suitable groups denoted by $R^{13}$ include unsubstituted and substituted alkyl, cycloalkyl and aryl (preferably phenyl) groups, and also unsubstituted and substituted hydrocarbon-carbonyl and hydrocarbonoxy-carbonyl groups, for example unsubstituted and substituted alkanoyl, cycloalkylcarbonyl, arylcarbonyl, alkoxycarbonyl, and aryloxycarbonyl groups. Examples of acyl groups $R^{13}$ include acetyl and benzyloxycarbonyl groups. Examples of unsubstituted alkyl groups $R^{13}$ include methyl, ethyl, n-propyl, isopropyl, n-butyl, sec-butyl, and tert-butyl groups. Examples of substituted alkyl groups $R^{13}$ include aralkyl (especially benzyl), alkoxyalkyl, alkenyloxyalkyl, alkynyloxyalkyl, aryloxyalkyl, arylalkoxyalkyl, alkoxyalkoxyalkyl (for example β-methoxyethoxymethyl), alkylthioalkyl, alkenylthioalkyl, alkynylthioalkyl, arylthioalkyl, aralkylthioalkyl, haloalkyl, formylalkyl, carboxyalkyl and salts and esters thereof, thiocyanotoalkyl, cyanoalkyl, acylalkyl, carbomoylalkyl, and aminoalkyl groups; each of the said alkyl, alkenyl and alkynyl moieties suitably having up to 6 carbon atoms; each of the said thio derivatives optionally being oxidised to the corresponding sulphoxide or sulphone derivative; and the said amino moiety of the said aminoalkyl groups suitably being of the formula V:

$$\begin{array}{c} R^{14} \\ | \\ -N \\ | \\ R^{15} \end{array} \qquad \text{V}$$

in which each of $R^{14}$ and $R^{15}$, which may be identical or different, denotes hydrogen or an unsubstituted or substituted hydrocarbon group, advantageously an alkyl group, preferably having from 1 to 6 carbon atoms, or $R^{14}$ and $R^{15}$ and the nitrogen atom to which they are attached together denote an unsubstituted or substituted, unsaturated or saturated heterocyclic ring, optionally containing one or more heteroatoms additional to the said nitrogen atom, each of $R^{14}$ and $R^{15}$ preferably denoting a hydrogen atom.

Erythromycin oximes and substituted oximes having 9-substituents of the type described above have been described in, for example, GB No. 1,100,504, E. H. Massey et al, G. H. Timms et al, U.S. Pat. Nos. 3,681,326, 3,869,445, 4,063,014 and 4,349,545, all op. cit.

The erythromycin oxime and substituted oxime derivatives according to the invention can exist in two geometric isomeric forms about the C=N double bond at the 9-position, as indicated by the wavy line in formula IV above, namely the E-form and the Z-form. The E-form is generally preferred.

In the case of the erythromycin imine derivatives according to the invention, $R^1$ and $R^2$ together denote a group of the formula VI:

$$=N\text{---}H \qquad \text{VI}$$

or one of $R^1$ and $R^2$ denotes an amino group, and the other of $R^1$ and $R^2$ together with $R^5$ denotes an ether oxygen atom. These two alternatives constitute different tautomeric forms of the imine derivative, which may exist in equilibrium.

Erythromycin imine has been described, for example, in G. H. Timms et al, op. cit.

In the case of the erythromycylamine derivatives according to the invention, one of $R^1$ and $R^2$ denotes hydrogen and the other of $R^1$ and $R^2$ may denote a group of the formula V above, in which $R^{14}$ and $R^{15}$ are defined as above. Suitably each of $R^{14}$ and $R^{15}$ denotes a hydrogen atom. Erythromycylamine and derivatives thereof have, for example, been described in GB No. 1,100,504, E. H. Massey et al and G. H. Timms et al, all op. cit.

The erythromycylamine derivatives according to the invention can exist in two isomeric forms at the 9-position, namely the (9R)-form, in which $R^1$ denotes hydrogen and $R^2$ denotes the optionally substituted amino group, and the (9S)-form, in which $R^1$ denotes the optionally substituted amino group and $R^2$ denotes hydrogen. The (9S)-isomer is preferred.

The erythromycin derivatives according to the invention are characterised by an 11-ether group, denoted as $-OR^3$ in the general formula I.

$R^3$ denotes a hydrocarbonoxymethyl, acyloxymethyl, acylaminomethyl or sulphonamidomethyl group of the formula II defined above. Examples of 11-O substituents of the formula II include those of the following formulae:

$$R^A\text{---}O\text{---}CH_2\text{---} \qquad \text{IIA}$$

$$R^B\text{---}CO\text{---}O\text{---}CH_2\text{---} \qquad \text{IIB}$$

$$R^B\text{---}CO\text{---}NH\text{---}CH_2\text{---} \qquad \text{IIC}$$

$$R^A\text{---}SO_2\text{---}NH\text{---}CH_2\text{---} \qquad \text{IID}$$

$$R^A\text{---}O\text{---}\underset{R^E}{\underset{|}{CH}}\text{---} \qquad \text{IIE}$$

$$R^B\text{---}CO\text{---}O\text{---}\underset{R^E}{\underset{|}{CH}}\text{---} \qquad \text{IIF}$$

$$R^B\text{---}CO\text{---}\underset{R^E}{\underset{|}{N}}\text{---}CH_2\text{---} \qquad \text{IIG}$$

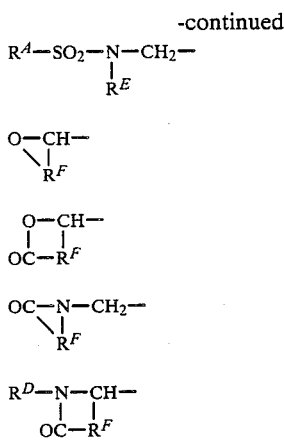

$$R^A-SO_2-N-CH_2- \quad \text{IIH}$$
$$\phantom{R^A-SO_2-N-}|$$
$$\phantom{R^A-SO_2-N-}R^E$$

$$O-CH- \quad \text{IIJ}$$
$$\phantom{O-}\backslash|$$
$$\phantom{O-CH}R^F$$

$$O-CH- \quad \text{IIK}$$
$$|\phantom{-}|$$
$$OC-R^F$$

$$OC-N-CH_2- \quad \text{IIL}$$
$$\phantom{OC-}\backslash|$$
$$\phantom{OC-N-}R^F$$

$$R^D-N-CH- \quad \text{IIM}$$
$$\phantom{R^D-}|\phantom{-N}|$$
$$\phantom{R^D-}OC-R^F$$

in which formulae
$R^A$, $R^B$ and $R^D$ are defined as above,
$R^E$ denotes an unsubstituted or substituted hydrocarbon group, and
$R^F$ denotes a unsubstituted or substituted, divalent, hydrocarbon group completing a 4- or 7-membered ring.

Suitably, the 11-O-substituent $R^3$ is of the formula IIA, IIC, IIG or IIL. Also suitably, $R^3$ may be of the formula IIB, IID or IIH.

Suitably, $R^A$ denotes an unsubstituted or substituted alkyl, alkenyl, aryl, or cyloalkyl group. Suitably, $R^B$ denotes a hydrogen atom or an unsubstituted or substituted alkyl, alkoxy, aryl, aryloxy, cycloalkyl, or cycloalkyloxy group. Suitably, the alkyl group $R^A$ or $R^B$ is a $(C_{1-6})$alkyl group, for example a methyl, ethyl, propyl or butyl group, especially a methyl or ethyl group. Suitably, the aryl group $R^A$ or $R^B$ may be a phenyl group, and the aryloxy group $R^B$ may be a phenoxy group. The cycloalkyl group or moiety suitably has from 3 to 7 carbon atoms, for example a cyclohexyl group or moiety.

Examples of substituents for substituted hydrocarbon groups $R^A$ or $R^B$ and for substituted hydrocarbon-oxy groups $R^B$ include hydroxy, halogen, carboxy, alkoxy, aryloxy, formyl, formyloxy, acyloxy (for example, alkanoyloxy and arylcarbonyloxy, especially benzoyloxy), alkoxycarbonyl, hydrocarbon-sulphonyloxy (for example, alkanesulphonyloxy), substituted-silyloxy (for example, trialkylsilyloxy), amino (which may suitably be of the formula V above, for example N-alkylamino and N,N-dialkylamino), oxo, azido, diazo, and heterocyclyl (especially nitrogen-containing heterocyclyl bonded through a ring nitrogen atom, for example triazolyl, piperidinyl, and phthalimido, and also heteroaryl) groups.

Suitably, $R^C$ denotes a hydrogen atom. Suitably, $R^D$ denotes an alkyl group (especially a methyl group) or a hydrogen atom. In the event that $R^C$ and/or $R^D$ denotes an unsubstituted or substituted hydrocarbon group, it may advantageously be an unsubstituted or substituted alkyl, cycloalkyl or aryl group. Suitably, the alkyl group is a $(C_{1-6})$alkyl group, for example a methyl or ethyl group. Suitably, the aryl group may be a phenyl group. The cycloalkyl group suitably has from 3 to 7 carbon atoms, for example the cyclohexyl group.

An example of a substituted alkyl group is an aralkyl group, for example a benzyl group. Suitably $R^C$ and/or $R^D$ denotes an alkyl group.

The above list of advantageous and suitable groups also applies to the hydrocarbon groups RE. Suitably RE denotes a methyl group.

In the event that two of $R^A$, $R^B$, $R^C$ and $R^D$ together denote, or RF denotes, a divalent, unsubstituted or substituted, organic group completing a 4- to 7-membered heterocyclic ring, the said ring may be saturated or unsaturated and may optionally contain hetero-atoms additional to those shown in the respective formula. Such additional hetero-atoms suitably include oxygen, sulphur, and nitrogen atoms. Suitably, two of $R^A$, $R^B$, $R^C$ and $R^D$ together denote, or RF denotes, an alkylene group, for example an ethylene, propylene or butylene group. For example, the group of the formula IIJ may be a tetrahydrofuryl group, and the group of the formula IIL may be a pyrrolid-2-on-1-ylmethyl group.

Further examples of suitable substituents for a hydrocarbon group $R^A$ to $R^E$, a hydrocarbon-oxy group $R^B$, and a divalent organic group denoted by two of $R^A$, $R^B$, $R^C$ and $R^D$ or by $R^F$, include, in particular, alkoxy, alkoxyalkoxy, aryloxy, hydroxy, amino, substituted amino (for example, monoalkylamino and dialkylamino), carboxy, esterified carboxy (for example, alkoxycarbonyl), acyloxy (for example, alkanoyloxy), carbamoyl ($H_2N-C(=O)-$), and substituted carbamoyl (for example, N-alkylcarbamoyl and N,N-dialkylcarbamoyl) groups. Any aryl or alkyl moiety in such substituents may itself be substituted by, for example, an alkyl or aryl group or one of the listed substituents, and any alkyl moiety advantageously contains not more than 6, preferably not more than 4, carbon atoms. An example of a substituent in which an alkyl moiety is itself substituted is an alkoxyalkoxy substituent.

Particularly preferred groups of the formula II are those of the formula IIA, especially those in which $R^A$ denotes a 2-substituted-ethyl or 3-substituted propyl group, wherein the substituent may, for example, 2 be one of the substituents listed above as a suitable substituent for the group $R^A$, including, for example, amino, N-alkylamino, N,N-dialkylamino, halogen, hydroxy, alkoxy, benzoyloxy, alkanesulphonyloxy, trisilyloxy, alkoxycarbonyl, alkanoyloxy, phenoxy, and heterocyclyl groups.

In the compounds of the general formula I, the 12-substituent denoted by $R^4$ is preferably a hydroxy group as in the erythronolide A ring, or, in other words, the compounds of the general formula I are preferably derivatives of erythromycin A. Alternatively, however, the present compounds may be derivatives of erythromycin B, in which case $R^4$ denotes a hydrogen atom, or of another naturally occurring erythromycin.

The 6-position of the erythronolide ring may carry a hydroxy group or an etherified hydroxy group, $R^5$, in which $R^5$ denotes hydroxy or alkoxy. Suitably, the 6-position carries a hydroxy group, as in naturally-occuring erythromycins.

In the event that the 6-position carries an etherified hydroxy group, the alkoxy group is advantageously a $(C_{1-6})$alkoxy group, preferably a methoxy group. 6-O-alkyl-erythromycin derivatives have been described in EP Nos. 0,041,355 A1 and 0,080,818 A1, both op. cit.

The $-OR^7$ group in the 3″-position of the cladinose ring may be a hydroxy group or a methoxy group. Preferably, $R^7$ denotes a methyl group as in erythromycin A and B.

The 4″-position of the cladinose ring may suitably carry a hydroxy group as in erythromycin A and B ($R^8=H$; $R^9=OH$). Various modifications of the 4″- position of the cladinose ring have previously been described and those modifications may be incorporated in the compounds according to the present invention:
(i) 4''-deoxy-4''-oxo derivatives ($R^8+R^9=O=$) are described in U.S. Pat. Nos. 3,842,069, 3,884,903 and 4,150,220, all op. cit.;
(ii) 4''-epi-hydroxy derivatives ($R^8=OH$; $R^9=H$) and 4''-deoxy-4''-alkanoyloxy-4''-epi derivatives ($R^8$=alkanoyloxy, especially $CH_3COO-$; $R^9=H$) are described in U.S. Pat. No. 3,884,903, op. cit.;
(iii) 4''-O-alkyl derivatives ($R^8$ or $R^9$=alkoxy, especially methoxy; the other of $R^8$ and $R^9=H$) are described in EP No. 0,080,818 A1, op. cit.;
(iv) 4''-deoxy-4''-amino derivatives ($R^8$ or $R^9$=amino or substituted amino; the other of $R^8$ and $R^9=H$) are described in U.S. Pat. No. 4,150,220, op. cit.;
(v) 4''-deoxy-4''-oxime derivatives ($R^8+R^9$=oxime (=N—OH) or substituted oxime, especially acetyloxime (=N—O—CO—$CH_3$)) are also described in U.S. Pat. No. 4,150,220, op cit.;
(vi) 4''-O-sulphonyl derivatives ($R^8=H$, $R^9=R^{12}-SO_2-O-$) are described in U.S. Pat. Nos. 3,836,519, 3,869,445 and 4,063,014 (all R. Hallas et al; Abbott Laboratories); and
(vii) 4''-deoxy derivatives ($R^8=R^9=H$) are described in JP No. 58-049396 (Toyo Jozo KK).

In the 4''-deoxy-4''-(substituted anino) derivatives, the substituted amino group $R^8$ or $R^9$ may suitably be a group of the formula $$-NHCOR^{16} \text{ or } -NHSO_2R^{16}$$

in which $R^{16}$ denotes a hydrocarbon group. In the 4''-O-sulphonyl derivatives, in which $R^8$ or $R^9$ denotes a sulphonyloxy group of the formula $$R^{12}-SO_2-O-,$$

the organic group $R^{12}$ may suitably be an unsubstituted or substituted hydrocarbon, oxahydrocarbon, thiahydrocarbon or azahydrocarbon group, more especially an alkyl, alkenyl, unsubstituted or substituted aryl (especially phenyl, nitrophenyl, halophenyl or alkylphenyl), unsubstituted or substituted aralkyl (especially benzyl, nitrobenzyl, halobenzyl or alkylbenzyl), unsubstituted or substituted aryloxyalkyl (especially phenoxyalkyl, nitrophenoxyalkyl, halophenoxyalkyl or alkylphenoxyalkyl), or substituted ethyl (especially $R^{17}-CH_2-CH_2-$, wherein $R^{17}$ is defined as below) group.

Examples of groups $R^{17}$ in the 4''-substituent $$R^{17}-CH_2-CH_2-SO_2-O-$$

include amino, substituted amino, carbamoyl, substituted carbamoyl, sulphamoyl, substituted sulphamoyl, substituted ureido, substituted thioureido, alkoxy, alkylthio, optionally substituted aryloxy, optionally substituted arylthio, optionally substituted benzyloxy, optionally substituted benzylthio, substituted suphonyl, substituted sulphinyl, substituted alkyl, substituted alkanoyl, substituted cyano, and other groups more specifically described in U.S. Pat. Nos. 3,869,445 and 4,063,014, op. cit.

Preferably, $R^{12}$ denotes a hydrocarbon group, particularly a ($C_{1-6}$)alkyl group, especially a methyl group.

The present invention includes pharmaceutically acceptable esters, especially in vivo hydrolysable esters, of the compounds of the general formula I. The esters may be formed at any hydroxy group in the compounds of the general formula I, but usually the ester will be formed at the 2'-hydroxy group of the desosamine ring, thus giving a 2'-O-acyl derivative of the type described in U.S. Pat. No. 2,862,921 (R. E. Booth et al; Upjohn Co.), U.S. Pat. No. 2,993,833 (V. C. Stephens; Eli Lilly), U.S. Pat. Nos. 3,836,519, 3,842,069, 3,869,445, 3,884,903, 3,884,904 and 4,150,220, all op. cit.

Suitable pharmaceutically acceptable in vivo hydrolysable esters include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include acetates, propionates, butyrates, acrylates, and ethylsuccinates.

The present invention also includes acid addition salts, especially pharmaceutically acceptable acid addition salts, of the compounds of the general formula I. Such acid addition salts may, in particular, be formed at the 3'-dimethylamino group of the desosamine ring.

Various acid addition salts of erythromycin are described in U.S. Pat. No. 2,761,859 (C. E. Hoffhine, Jr.; Abbott Laboratories) and U.S. Pat. No. 2,852,429 (J. T. Shepler; Eli Lilly).

Suitable acid addition salts of the compounds of the invention include pharmaceutically acceptable inorganic acid addition salts, for example the sulphate, nitrate, phosphate, borate, hydrochloride and hydrobromide, and also pharmaceutically acceptable organic acid addition salts, for example the acetate, tartrate, maleate, citrate, succinate, benzoate, ascorbate, methane-sulphate, α-keto-glutarate, α-glycerophosphate, and glucose-1-phosphate. Preferably the acid addition salt is the laurylsulphate salt.

Examples of individual compounds according to the present invention include the title compounds of the examples as well as
corresponding 6-ether derivatives, and
corresponding derivatives in which the 4''-position is modified as discussed above;
and also
pharmaceutically acceptable esters and acid addition salts of such compounds.

The 11-ether erythromycin derivatives or erythromycin 9-substituted-oxime derivatives according to the invention may be prepared by reacting erythromycin or an erythromycin 9-oxime or 9-substituted-oxime derivative having a hydroxy substituent at the 11-position, in which any reactive groups (other than the 11-hydroxy group) may optionally be protected, with a suitable alkylating agent $R^3$-X; and thereafter if necessary carrying out one or more of the following steps:
(a) converting a substituent on the erythromycin structure to another such substituent in a conventional manner;
(b) removing any protecting groups; and
(c) forming a pharmaceutically acceptable ester or acid addition salt.

A resulting 9-oxo compound according to the invention may, if desired, optionally be converted to a 9-oxime or 9-substituted-oxime compound according to the invention.

A resulting 9-substituted-oxime compound according to the invention may, if desired, subsequently be converted to a 9-oxo or 9-oxime compound according to the invention. A resulting 9-oxime compound may, in turn, be converted to a 9-imino compound according to the invention, which may, if desired, be further converted into a 9-amino compound according to the invention, which may, if desired, be yet further converted to a 9-substituted-amino compound according to the invention.

More particularly, a compound of the general formula I as hereinbefore defined or a pharmaceutically acceptable ester or acid addition salt thereof may be prepared by a process which comprises reacting a pound of the general formula VII:

VII

[Chemical structure diagram showing erythromycin-like macrolide with substituents $R^{18}$, $R^5$, $R^4$, $R^7$, $R^8$, $R^9$, CH$_3$ groups, $C_2H_5$, $N(CH_3)_2$, HO, and OR$^7$]

wherein
$R^4$, $R^5$, $R^7$, $R^8$ and $R^9$ are defined as above with respect to general formula I, and
$R^{18}$ denotes an oxo group, an oxime group, or a substituted oxime group,
in which compound of the general formula VII any reactive group (other than the 11-hydroxy group) may optionally be protected, with an alkylating agent of the general formula VIII:

$$Q-\underset{R^C}{\overset{|}{C}H}-X \qquad \text{VIII}$$

in which
Q and $R^C$ are as defined above, and
X denotes a leaving group;
to give a compound of the general formula I in which $R^1$ and $R^2$ together denote an oxo group or a substituted oxime group;
and thereafter, if necessary or desired, carrying out one or more of the following steps in any suitable order:

(a) converting an oxo group denoted by $R^1$ and $R^2$ together to an oxime group or a substituted oxime group;
(b) converting a substituted oxime group denoted by $R^1$ and $R^2$ together to an oxo group (or the corresponding tautomer), another substituted oxime group, or an oxime group;
(c) converting a resulting oxime group denoted by $R^1$ and $R^2$ together to an oxo group (or the corresponding tautomer), a substituted oxime group or an imino group (or the corresponding tautomer);
(d) converting a resulting imino group denoted by $R^1$ and $R^2$ together to an amino group denoted by $R^1$ or $R^2$;
(e) converting a resulting amino group denoted by $R^1$ or $R^2$ to a substituted amino group;
(f) converting any one or more of the groups denoted by $R^3$, $R^5$, $R^8$ and $R^9$ to another such group;

(g) removing any protecting group that may be present; and
(h) forming a pharmaceutically acceptable ester or acid addition salt.

The compound of the general formula VII in which:
each of $R^4$, $R^5$ and $R^9$ denotes hydroxy,
$R^8$ denotes hydrogen, and
$R^7$ denotes methyl, and
$R^{18}$ denotes oxo
is naturally occurring erythromycin A, and the compound of the general formula VII in which:
each of $R^4$ and $R^8$ denotes hydrogen, and
each of $R^5$ and $R^9$ denotes hydroxy,
$R^7$ denotes methyl,
$R^{18}$ denotes oxo
is naturally occurring erythromycin B.

The corresponding compounds in which $R^{18}$ denotes oxime or substituted oxime are erythromycin A or B 9-(substituted)oximes, and may be prepared from erythromycin A or B by known methods, for example by the methods described in the above-cited references relating to erythromycin 9-oximes and 9-substituted-oximes.

Other compounds of the general formula VII may also be prepared, by methods known per se, from erythromycin A or B or the corresponding 9-oxime or 9-oxime etherderivative. For example, a compound in which the 4''-position is substituted other than as in naturally-occuring erythromycin A or B (that is to say, in which $R^8$ is other than hydrogen and/or $R^9$ is other than hydroxy) may be prepared as described in the respective references cited above.

In general, in the preparation of compounds of the general formula VII in which $R^{18}$ denotes a (substituted) oxime group, the conversion of the 9-oxo group of erythromycin A or B to a 9-oxime or 9-substituted-oxime group may be effected prior to or subsequent to modification of other positions of the erythromycin molecule.

Prior to carrying out the reaction of a compound of the general formula VII with the alkylating agent, any reactive group of the compound of the general formula VII (other than the 11-hydroxy group) may optionally be protected in a known manner.

In particular, the 3'-dimethylamino group will generally be protected by an N-protecting group. The N-protection may be effected in known manner, for example by the method described by E. H. Flynn et al, (*J. Amer. Chem. Soc.*, 1955, 77, 3104–3106).

Examples of suitable N-protecting groups include benzyloxycarbonyl, and substituted benzyloxycarbonyl, (for example, p-methylbenzyloxycarbonyl p-nitrobenzyloxycarbonyl, p-bromobenzyloxycarbonyl, p-phenylazobenzyloxycarbonyl, and p-(p'-methoxyphenylazo)-benzyloxycarbonyl). A preferred N-protecting group is benzyloxycarbonyl. It may also be advantageous to protect one or more of the hydroxy groups present in the erythromycin molecule (other than the 11-hydroxy group) prior to reaction. In particular, it may be advantageous to protect any hydroxy groups present at the 2'- and 4''-positions, especially the 2'-hydroxy group. It is convenient to employ the same group to protect the hydroxy group(s) as that employed to protect the amino moiety, especially a benzyloxycarbonyl group.

Any reactive substituents that may be present in the group $R^8$ or $R^9$ should preferably also be protected in a conventional manner.

The present invention also provides compounds of the general formula IX, which are useful as intermediates in the preparation of the compounds of the general formula I:

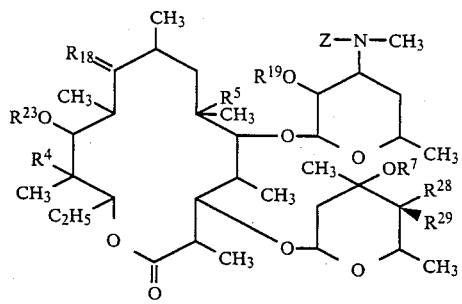

$R^4$, $R^5$, $R^7$ and $R^{18}$ are defined as above;
$R^{19}$ denotes H or Z;
$R^{23}$ denotes H or, preferably, $R^3$ (where $R^3$ is defined as above), with the proviso that, if $R^{18}$ denotes oxo or $R^5$ denotes methoxy, then $R^{23}$ denotes $R^3$;
one of $R^{28}$ and $R^{29}$ denotes H, OH, OZ, $NZ_2$, $NH_2$, NHZ, substituted $NH_2$, substituted NHZ, alkoxy, alkanoyloxy, or $R^{12}$—$SO_2$—O— (in which $R^{12}$ denotes an organic group), and the other of $R^{28}$ and $R^{29}$ denotes H, or
$R^{28}$ and $R^{29}$ together denote oxo; and
Z denotes a protecting group, more particularly an N-protecting group, preferably a substituted benzyloxycarbonyl group or, especially, a benzyloxycarbonyl group.

Suitably, $R^{23}$ denotes $R^3$.

In the process according to the invention, the erythromycin compound of the general formula VII, optionally containing protective groups, is reacted with an alkylating agent of the general formula VIII, suitably in the presence of a base and an organic solvent.

The alkylating agent may be represented by the general formula VIIIA:

 $R^3$—X  VIIIA in which
$R^3$ denotes a group of the formula II given above, and
X denotes a leaving group.

Examples of suitable leaving groups X include halogen atoms (for example chlorine, bromine, and iodine), alkylsulphonyloxy groups (for example methanesulphonyloxy), and arylsulphonyloxy groups (for example p-toluenesulphonyloxy). Preferably, X denotes a halogen atom, especially chlorine atom.

The alkylation reaction used according to the process of the invention is a novel alkylation procedure in relation to erythromycins and can be carried out under more mild conditions than can alkylation methods previously used to etherify erythromycin hydroxy substituents, such as the alkylation procedures described in U.S. Pat. Nos. 3,842,069, 3,884,904, EP Nos. 0,041,355 A1, 0,080,818 A1, and 0,080,819 A1, all op. cit. It has been found that alkylation according to the process of the invention results in etherification preferentially at the 11-hydroxy group.

The alkylating agent used according to the present invention is suitably a derivative of an alkyl halide. Particularly suitable alkylating agents of that type include, for example, α-haloalkyl ethers (such as compounds in which $R^3$ is of the formula IIA, IIE or IIJ), especially α-chloroalkyl ethers; α-haloalkyl esters (such as compounds in which $R^3$ is of the formula IIB, IIF or IIK), especially α-chloroalkyl esters; and α-haloalkyl amides (such as compounds in which $R^3$ is of the formula IIC, IIG, IIL or IIM), especially α-chloroalkyl amides.

The alkylation reaction is conveniently carried out under weakly basic conditions. The base is suitably an organic base, advantageously a non-nucleophilic organic base, also advantageously a weak organic base. Particularly suitable organic bases include tertiary amines, for example N,N-diisopropyl-ethylamine and substituted pyridines, especially alkylpyridines, for example dimethylpyridines (i.e. lutidines, e.g. 2,6-lutidine) and trimethylpyridines (i.e. collidines).

If the group $R^3$ contains any reactive substituents, that is to say, substituents that will react under the above-mentioned conditions, (including, for example, some of the substituents mentioned previously for the group $R^3$), such substituents may advantageously be protected in conventional manner prior to reaction of the alkylating agent with the erythromycin compound of the general formula VII.

The alkylation reaction may suitably be carried out in an inert solvent. Suitable solvents include, for example, N,N-dimethylformamide, N,N-dimethylacetamide, dimethylsulphoxide, hexamethylphosphoric triamide, N-methylpyrrolidinone, tetrahydrofuran, dioxan, dichloromethane, ethoxyethane, and 1,2-dimethoxyethane, and also mixtures of two or more such solvents. The alkylation reaction may suitably be carried out using from 1 to 6 moles, preferably from 1 to 5 moles, of the alkylating agent per mole of the erythromycin compound of the general formula VII. The base is suitably used in a molar excess with respect to the alkylating agent, advantageously an excess of at least 1.1:1, preferably from 1.5:1 to 2:1.

The said reaction may suitably be effected at a cool to slightly elevated temperature preferably at about ambient temperature. The reaction may, for example, be effected at a temperature within the range of from $-20°$ C. to $+50°$ C., preferably from $0°$ C. to $+35°$ C., especially from $+15°$ C. to $+30°$ C. If the initial erythromycin compound of the general formula VII contains a 9-oxime group, that group will react with the alkylating agent to form a 9-oxime ether. Alternatively, the 9-oxime group may first be protected by means of, for example, an ether or ester group, so that the alkylation reaction is in fact carried out on a 9-substituted-oxime. Such protection may be effected in known manner using known ether-forming hydroxy-protecting groups, for example benzyl, substituted benzyl, tetrahydropyranyl, and trichlorethyl groups.

Accordingly, the erythromycin compound resulting from the alkylation reaction will contain a 9-oxo group (if the starting compound of the general formula VII contained such a group) or a 9-substituted-oxime group (if the starting material contained a 9-oxime or 9-substituted-oxime group). If the desired product of the general formula I contains such a group, no reaction need be carried out at the 9-position, although a 9-oxo group may optionally now be converted into a 9-oxime or 9-substituted-oxime group, and a 9-substituted-oxime group may optionally now be converted into a 9-oxo or 9-oxime group or into another 9-substituted-oxime group. If the desired product of the general formula I contains a 9-imino group, such a group may be obtained by conversion of a 9-oxo or 9-oxime group, and a 9-imino group may in turn be converted to a 9-(optionally substituted)-amino group.

All such conversions at the 9-position may be carried out in known manner, for example as described in the above-cited references. For example, the oxime may be converted to the imine by reaction with titanium trichloride in known manner, and the imine may be converted to the amine by reaction with sodium borohydride in known manner.

Also after completion of the alkylation reaction, and prior or subsequent to any conversion of the 9-substituent, any of the groups $R^5$, $R^8$ and $R^9$ may be converted to any of the other such groups within the definitions given above by methods known in the art, for example by the methods disclosed in the above-cited references. For example, a compound in which $R^9$ denotes hydrogen and $R^8$ denotes hydroxy can be converted to a compound in which $R^8$ and $R^9$ together denote oxo and optionally thereafter to a compound in which $R^9$ denotes hydroxy or acetoxy and $R^8$ denotes hydrogen by methods analogous to those described in U.S. Pat. No. 3,884,903, op. cit.

Moreover, the group $R^3$ introduced by the alkylation reaction according to the invention may, at this stage, be converted to another group $R^3$ in a manner known per se. In particular, a substituent in the group $R^3$ may be converted to or replaced by another substituent using conventional techniques; for example, an azido substituent may be converted into, or a halo substituent may be replaced by, an amino or substituted amino (including N-bonded heterocyclyl) substituent.

After completion of the alkylation reaction, any protecting groups may be removed by a conventional method. It is preferable to employ a hydrogenation procedure.

The hydrogenation may suitably be carried out in the presence of a transition metal catalyst, for example palladium, which may, for example, be in the form of palladium on carbon (charcoal), palladium on barium sulphate, palladium on calcium carbonate, or palladium black. A favoured catalyst is palladium on carbon (sometimes referred to as palladium on charcoal); for example 5%, 10%, 20% or 30% palladium on carbon. A low, medium or high pressure of hydrogen may be used in this reaction, for example a pressure of from 1 to 6 atmospheres absolute, a pressure of 1 atmosphere absolute being convenient. The reaction may suitably be carried out at a non-extreme temperature, for example at a temperature within the range of from 0° C. to 30° C., preferably from 12° C. to 25° C. It is generally convenient to carry out the reaction at ambient temperature. The reaction is preferably carried out at a pH within the range of from 4.5 to 5.0, which may be maintained by the use of a suitable buffer, for example an acetate buffer at pH 4.8.

Suitable solvents for carrying out the hydrogenation include ethanol, n-propanol, isopropanol, tetrahydrofuran, dioxan, ethyl acetate, a mixture of two or more such solvents, or such a solvent or mixture in the presence of water. A favoured solvent is ethanol.

In order to restore the dimethylamino group at the 3'-position, it is convenient to effect a reductive methylation, which advantageously may be carried out at the same time as the reductive removal of the protecting groups, as in the method of Flynn et al, op. cit.

A compound of the general formula I may be converted to a pharmaceutically acceptable salt thereof or ester thereof in a conventional manner at any convenient stage in the manufacturing process, for example before or after the removal of any protecting groups and/or before or after any conversion of the 9-substituent and/or of groups $R^5$, $R^8$ and $R^9$ to other such groups.

Isolation and purification of a compound according to the invention may be carried out using conventional methods, and may include a chromatography step. Preferably the product is isolated in crystalline form.

The compounds according to the invention, that is to say, the compounds of the general formula I and their pharmaceutically acceptable salts and esters, have antibacterial properties and are useful for the treatment of bacterial infections in animals, especially mammals, including humans, in particular humans and domesticated animals (including farm animals). The compounds may be used for the treatment of infections caused by a wide range of gram-positive and gram-negative organisms including, for example, *Bacillus subtilis, Corynebacterium xerosis, Sarcina lutea, Stahylococcus aureus, Streptococcus faecalis, Streptococcus pyogenes, Streptococcus agalactiae, Streptococcus pneumoniae, Haemophilus sp. Neisseria sp., Chlamydia sp.,* and *Legionella sp.*

The present invention provides a pharmaceutical composition comprising a compound according to the invention together with a pharmaceutically acceptable carrier or excipient.

The present invention also provides a method of treating bacterial infections in animals, especially in humans and in domesticated mammals, which comprises administering a compound or composition according to the invention to a patient in need thereof.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colouring agents.

A compound or composition according to the invention may suitably be administered to the patient in an antibacterially effective amount. A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.5 to 50 mg/kg of body weight. For an adult human (of approximately 70 kg body weight), from 100 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferably from 50 to 500 mg, of a compund according to the invention.

No adverse toxicological effects are indicated when the compounds according to the invention are administered within the above-mentioned dosage ranges.

The following examples illustrate the preparation of compounds according to the present invention. The starting materials used in the examples were prepared as described in Preparations 1 to 6 preceding the examples.

PREPARATION 1

2'-O,N-Dibenzyloxycarbonyl-des-N-methylerythromycin A 9-methoxime (a) Erythromycin A 9-methoxime Erythromycin A (25 g), O-methyl-hydroxylamine hydrochloride (12.5 g) and anhydrous sodium acetate (12.5 g) were added to dry methanol (250 ml) and the mixture was refluxed for 16 hours. The methanol was removed and the resulting solid was dissolved in chloroform (500 ml) and washed with 10% aqueous $Na_2CO_3$ solution (4×50 ml), brine (100 ml) and dried ($MgSO_4$). The solvent was removed and the resulting solid was recrytallised from chloroform to give erythromycin A 9-methoxime (17.4 g) as colourless needles; m.p. 128°–130° C. (dichloromethane/petrol (60°–80° C.)); $[\alpha]_D^{20}$ −62.8° (1.0% wt/vol in EtOH); $\nu_{max}$ ($CHCl_3$) 3425 and 1725 cm$^{-1}$; (Found: C, 59.32%; H, 9.12%; N, 3.5%. $C_{38}H_{70}N_2O_{13}$ requires C, 59.82%; H, 9.25%; N, 3.67%).

(b) 2'-O,N-Dibenzyloxycarbonyl-des-N-methylerythromycin A 9-methoxime

The product from Preparation 1(a) (22 g) was mixed with sodium bicarbonate (22.1 g) and stirred while benzyl chloroformate (79 ml) was added. The mixture was stirred at 55° C. for 3 hours and then added to dichloromethane (100 ml) and chromatographed to give the title compound (19.1 g) as colourless crystals, m.p. 115°–116° C. (ether/hexane); $[\alpha]_D^{20}$ −74.1° (1.0% wt/vol in $CHCl_3$); $\nu_{max}$ ($CHCl_3$) 1725 and 1690 cm$^{-1}$; (Found: C, 62.34%; H, 8.02%; N, 2.89%. $C_{53}H_{80}N_2O_{17}$ requires C, 62.58%; H, 7.93%, N, 2.75%.

PREPARATION 2

2'-O,N-Dibenzyloxycarbonvl-des-N-methylerythromycin A 9-0-benzyloxycarbonyloxime Erythromycin A 9-oxime (12.9 g, 17.3 mmol), sodium bicarbonate (12.9 g, 154 mmol) and benzyl chloroformate (38 ml, 266 mmol) were thoroughly mixed and then 10 heated, with vigorous stirring, at 50° C. for 90 minutes. After cooling, the solution was diluted with an equal volume of dichloromethane then applied to a silica gel column (100 g) made up in, and eluted with, ethyl acetate/hexane (1:1). The title compound was obtained as a colourless foam which was crystallised from ether/hexane to give a white solid, m.p. 118°–119° C., $[\alpha]_D^{20}$ −106.2° (1% wt/vol in $CHCl_3$); $\nu_{max}$ 3450, 1750, 1700, 700 cm$^{-1}$; mass spectrum FAB-MS MH+ 1137 ($C_{60}H_{85}N_2O_{19}$).

PREPARATION 3

2'-O,N-Dibenzyloxycarbonyl-des-N-methylerythromycin A 9-oxime

The product from Preparation 2 (9.57 g, 8.42 mmol) was dissolved in methanol (250 ml) and triethylamine (10 ml) and water (25 ml) added. The mixture was heated at reflux for 2 h after which time the solvent was removed in vacuo and the residue partitioned between ethyl acetate and 10% aqueous sodium bicarbonate. The organic layer was separated and dried over $MgSO_4$. Solvent removal gave the crude material (7.85 g) which was purified by column chromatography (100 g silica, 60% ethyl acetate/hexane as eluent) to give the title compound (5.0 g, 5.0 mmol, 59%) which was recrystallised from ethyl acetate/hexane to give a white crystalline solid, m.p. 163°–164° C., $[\alpha]_D^{20}$ −84.6° (C 1.0, $CHCl_3$); $\nu_{max}$ ($CHCl_3$) 3550, 3480, 1750, 1700, 700 cm$^{-1}$.

PREPARATION 4

2-Bromoethyloxymethyl chloride 2-Bromoethanol (12.5 g) in dichloroethane (100 ml) was treated with paraforamldehyde (3.0 g) and excess hydrogen chloride gas for 1 h at 0° and a further 2 h at room temperature with stirring. The clear solution 3 was then evaporated under reduced pressure to give an oil which was evaporated from dry diethyl ether (2×100 ml) to give the title compound as an oil (15.1 g); $\nu_{max}$ (film) 650 cm$^{-1}$.

PREPARATION 5

2-Phenyloxyethyloxymethyl chloride

2-Phenoxyethanol (13.8 g) was converted into the title compound using a procedure analogous to that described in Preparation 4. The title compound was thus obtained as a colourless oil (12.6 g); $\nu_{max}$ 650 cm$^{-1}$.

PREPARATION 6

2-Phthalimidoethoxymethyl chloride

2-Phthalimidoethanol (6.37 g) was converted into the title compound by a procedure analogous to that described in Preparation 4. The title compound was obtained as a white solid (6.5 g), $\nu_{max}$ ($CHCl_3$) 1785, 1720 and 1705 cm$^{-1}$.

EXAMPLE 1

11-O-Methoxymethyl-erythromycin A 9-methoxime (a)

11-O-Methoxymethyl-2'-O,N-dibenzyloxycarbonyl-des-N-methylerythromycin A 9-O-methoxime 2'-O,N-Dibenzyloxycarbonyl-des-N-methylerythromycin A 9-methoxime (400 mg) in dry dimethylformamide (4 ml) was treated with chloromethyl methyl ether (0.08 ml) and 2,6-lutidine (0.20 ml) and the mixture stirred at room temperature for 1 h. The mixture was diluted with ethyl acetate (100 ml) and the organic layer washed successively with water, citric acid solution, saturated aqueous sodium bicarbonate solution, and finally brine. After drying over anhydrous magnesium sulphate, the solvent was evaporated. Chromatography of the residue on silica-gel using ethyl acetate/hexane (1:1) as eluent gave the title compound as a colourless foam (250 mg); $\nu_{max}$(CHCl$_3$) 1735 and 1690 cm$^{-1}$; mass spectrum FAB-MS MH+1061 ($C_{55}H_{85}N_2O_{18}$).

(b) 11-O-Methoxymethylerythromycin A 9-methoxime

The product from Example 1(a) (250 mg) was dissolved in a mixture of ethanol (15 ml) and acetate buffer (pH 4.8; 1.2 ml) and the solution shaken with 10% palladium/charcoal (100 mg) under 1 atmosphere of hydrogen for 30 min. 37% Formaldehyde (1.2 ml) was added and the hydrogenation continued for a further 1½ h. The catalyst was removed by filtration and washed with ethanol and water. The solvent was removed from the filtrate under reduced pressure and the residue was diluted to about 20 ml with water. The solution was brought to pH 11 with potassium carbonate and extracted with ethyl acetate (3×20 ml). Combined extracts were washed with water (20 ml) and dried over anhydrous magnesium sulphate. Evaporation gave the title compound as a colourless foam (164 mg); $[\alpha]_D^{20}$ −69.3° (1.0% wt/vol in CHCl$_3$); $\nu_{max}$ (CHCl$_3$) 1730 cm$^{-1}$; mass spectrum M+806.5162 ($C_{40}H_{74}N_2O_{14}$ requires M 806.5144).

EXAMPLE 2

11-O-[2-Benzoyloxyethoxymethyl]erythromycin A 9methoxime (a)

11-O-[2-Benzoyloxyethoxymethyl]-2'-O,N-dibenzyloxy carbonyl-des-N-methylerythromycin A 9-methoxime 2'-O,N-dibenzyloxycarbonyl-des-N-methylerythromycin A 9-O-methoxime (616 mg) in dry dimethylformamide (5 ml) was treated successively with 2,6-lutidine 0.35 ml) and 2-benzoyloxyethhoxyethylene (0.38 ml) and the mixture stirred at room temperature for 18 h. The solution was diluted with ethyl acetate (100 ml) and the organic layer washed successively with water, citric acid solution, saturated aqueous sodium bicarbonate solution, and finally brine. After drying over anhydrous magnesium sulphate, the solvent was evaporated. Chromatography of the residue on silica gel using dichloromethane/ethyl acetate (2:1) as eluent gave the title product as a colourless foam (400 mg) and recovered starting material (170 mg); $\nu_{max}$ (CHCl$_3$) 1725 cm$^{-1}$.

(b) 11-O-[2'-Benzoyloxyethoxymethyl]erythromycin A 9-methoxime

The product from Example 2(a) was converted into the title compound using a procedure analogous to that described in Example 1(b). The title compound was obtained as a colourless foam; $\nu_{max}$(CHCl$_3$) 1725 cm$^{-1}$; mass spectrum M+940.5547 ($C_{48}H_{80}N_2O_{16}$ requires M, 940.5512).

EXAMPLE 3

11-O-[2-Hydroxyethoxymethyl]erythromycin A 9-methoxime (a)

11-O-[2-Hydroxyethoxymethyl]-2'-O,N-dibenzyloxycarbonyl-des-N-methylerythromycin A 9-methoxime The product from Example 2(a) (422 mg) in methanol (10 ml) was treated with potassium carbonate (100 mg) and the mixture stirred at room temperature overnight. The solution was acidified using citric acid solution, toluene (80 ml) was added, and the mixture was stirred vigorously. The methanol was evaporated and the toluene solution washed with water (20 ml). After drying over anhydrous magnesium sulphate, the solvent was evaporated. Chromatography of the residue on silica gel using ethyl acetate/hexane as eluent gave the title product as a colourless foam (348 mg); $\nu_{max}$ (CHCl$_3$) 1725 and 1690 cm$^{-1}$; mass spectrum FAB-MS MH+1091 (CH$_{87}$N$_2$O$_{19}$).

(b) 11-O-[2-Hydroxyethoxymethyl]erythromycin A 9methoxime

The product from Example 3(a) was converted into the title compound using a procedure analogous to that described in Example 1(b). The title compound was obtained as a colourless foam; $\nu_{max}$ (CHCl$_3$) 3400 and 1720 cm$^{-1}$; mass spectrum M+836.5235 ($C_{41}H_{76}N_2O_{15}$ requires M 836.5249).

EXAMPLE 4

11-O-[2-Methanesulphonyloxyethoxymethyl]erythromycin A 9-methoxime (a)

11-O-[2-Methanesulphonyloxyethoxymethyl]-2'-O,N-dibenzyloxycarbonyl-des-N-methylerythromycin A 9-methoxime The product from Example 3(a) (700 mg) in dry pyridine (5 ml) was treated with methanesulphonyl chloride (0.053 ml) at 0°–5° C. and the mixture subsequently stirred at room temperature overnight. Pyridine was evaporated and the residue partitioned between ethyl acetate and water. The organic solution was washed with citric acid solution, saturated aqueous sodium bicarbonate, and finally brine. After drying over anhydrous magnesium sulphate, the solvent was evaporated. Chromatography on silica gel using ethyl acetate/hexane as eluent gave the title compound as a colourless foam (429 mg); $[\alpha]_D^{20}$ −98.4° (1.0% wt/vol in CHCl$_3$) $\nu_{max}$ (CHCl$_3$) 1730 and 1695 cm$^{-1}$; mass spectrum FAB-MS MH+1169 ($C_{57}H_{89}N_2O_{20}S$).

(b)

11-O-[2-Methanesulphonyloxyethoxymethyl]erythromycin A 9-methoxime

The product from Example 4(a) was converted into the title compound using a procedure analogous to that described in Example 1(b). The title compound was obtained as a colourless foam; $[\alpha]_D^{20}$ −79.6° (1.0% wt/vol in CHCl$_3$); $\nu_{max}$(CHCl$_3$) 1725 cm$^{-1}$; mass spectrum FAB-MS MH+915 ($C_{42}H_{79}N_2O_{17}S$).

EXAMPLE 5

11-O-Ethoxymethylerythromycin A 9-methoxime (a) 11-O-Ethoxymethyl-2'-O,N-dibenzyloxycarbonyldes-N-methylerythromycin A 9-methoxime 2'-O,N-Dibenzyloxycarbonyl-des-N-methylerythromycin A 9-methoxime (200 mg) in dry dimethylformamide (3 ml) was treated with 2,6-lutidine (0.18 ml), chloromethyl ethyl ether (0.06 ml) and the mixture stirred at room temperature for 2 h. Employing the same work-up procedure described in Example 1(a) the title compound was obtained as a colourless gum (195 mg); $[\alpha]_D^{20}$ −83.3° (1.0% wt/vol in CHCl$_3$), $\nu_{max}$ (CHCl$_3$) 1730 and 1695 cm$^{-1}$; mass spectrum M+1074.590 (C$_{56}$H$_{86}$N$_2$O$_{18}$ requires M 1074.5880).

(b) 11-O-Ethoxymethylerythromycin A 9-methoxime

The product from Example 5(a) was converted into the title compound by a procedure analogous to that described in Example 1(b). The title compound was thus obtained as a colourless foam; $[\alpha]_D^{20}$ −93.9° (1.0% wt/vol in CHCl$_3$); $\nu_{max}$ (CHCl$_3$) 1725 cm$^{-1}$; mass spectrum M+820.5307 (C$_{41}$H$_{76}$N$_2$O$_{14}$ requires M 820.5300).

EXAMPLE 6

11-O-[2-Trimethylsilyloxyethoxymethyl]-erythromycin A 9-methoxime (a) 11-O-[2-Trimethylsilyloxyethoxymethyl]-2'-O,N-dibenzyloxycarbonyl-des-N-methylerythromycin A 9-methoxime 2'-O,N-Dibenzyloxycarbonyl-des-N-methylerythromycin A 9-methoxime (200 mg) in dry dimethylformamide (4 ml) was treated with 2,6-lutidine (0.12 ml) and 2'-trimethylsilyloxyethoxymethyl chloride (0.12 ml) and the mixture stirred at room temperature for 2 h. Employing the same work-up procedure as described in Example 1(a) the title compound was obtained as a colourless foam (158 mg); $\nu_{max}$ (CHCl$_3$) 1725 and 1690 cm$^{-1}$; mass spectrum FAB-MS MH+1147 (C$_{59}$H$_{95}$N$_2$O$_{18}$Si).

(b) 11-O-[2'-Trimethylsilyloxyethoxymethyl]erythromycin A 9-methoxime

The product from Example 6(a) was converted into the title compound using a procedure analogous to that described in Example 1(b). The title compound was obtained as a colourless foam; $[\alpha]_D^{20}$ −81.3° (1.0% wt/vol in CHCl$_3$); $\nu_{max}$ (CHCl$_3$) 1730 cm$^{-1}$; mass spectrum M+892.5700 (C$_{44}$H$_{84}$N$_2$O$_{14}$Si requires M 892.5696).

EXAMPLE 7

11-O-[2-Methoxyethoxymethyl]erythromycin A 9-methoxime (a) 11-O-[2-Methoxyethoxymethyl]-2'-O,N-dibenzyloxycarbonyl-des-N-methylerythromyin A 9-methoxime 2'-0-N-Dibenzyloxycarbonyl-des-N-methylerythromycin A 9-methoxime (300 mg) in dry dimethylformamide (4 ml) was treated with lutidine (0.18 ml) and 2'-methoxyethoxymethyl chloride (0.11 ml) and the mixture stirred at room temperature overnight. Using the same work-up procedure as described in Example 1(a) the crude product was obtained. Chromatography on silica gel using ethyl acetate/hexane (2:1) as eluent gave the title compound as a colourless foam (178 mg); $\nu_{max}$ (CHCl$_3$) 1720 and 1690 cm$^{-1}$.

(b) 11-O-[2-Methoxyethoxymethyl]erythromycin A 9methyloxime

The product from Example 7(a) was converted into the title compound using a procedure analogous to that described in Example 1(b). The title compound was thus obtained as a colourless foam; $[\alpha]_D^{20}$ −98.9° (1.0% wt/vol in CHCl$_3$) 1720 cm$^{-1}$; mass spectrum M+850.5434 (C$_{42}$H$_{78}$N$_2$O$_{15}$ requires M, 850.5406).

EXAMPLE 8

11-O-[2-Benzoyloxyethoxymethyl]erythromycin A 9-oxime (a) 11-O-[2-Benzoyloxyethoxymethyl]-2'-O,N-dibenzyloxy-carbonyl-des-N-methylerythromycin A 9-benzyloxycarbonyloxime 2'-O,N-dibenzyloxycarbonyl-des-N-methylerythromycin A 9-benzyloxycarbonyloxime (3.24 g) in dry dimethylformamide (20 ml) was treated with 2,6-lutidine (1.75 ml) and 2-benzyloxyethoxymethylchloride (1.93 ml) and the mixture stirred at room temperature for 24 h. The solution was diluted with ethyl acetate (150 ml) and the organic solution washed successively with water, citric acid solution, aqueous sodium bicarbonate solution, and finally brine. After drying over anhydrous magnesium sulphate, the solvent was evaporated. Chromatography of the residue on silica gel using ethyl acetate/dichloromethane (1:2) as eluent gave the title product as a colourless foam (3.56 g); $\nu_{max}$ (CHCl$_3$) 1720 cm$^{-1}$.

(b) 11-O-[2-Benzoyloxyethoxmethyl]erythromycin A 9-oxime

The product from Example 8(a) (200 mg) in ethanol (12 ml) containing acetate buffer (1 ml; pH 4.8) was shaken with 10% Pd/C (70 mg) under 1 atmosphere of hydrogen for ½ h. 37% Formaldehyde (1 ml) was added and the hydrogenation continued for a further 1½ h. The catalyst was filtered off and the filtrate washed with ethanol. Evaporation gave a colourless oil. The residue was taken up in water (15 ml) and the solution brought to pH 11 with potassium carbonate. The aqueous solution was extracted with ethyl acetate (2×30 ml) and the extracts washed with water. After drying over anhydrous magnesium sulphate, the solvent was evaporated to give the title compound as a colourless foam (166 mg); $\nu_{max}$ (CHCl$_3$) 1720 cm$^{-1}$.

EXAMPLE 9

11-O-Methoxymethylerythromycin A 9-oxime (a) 11-O-Methoxymethyl-2'-O,N-dibenzyloxycarbonyl-des-N methylerythromycin A 9-benzyloxycarbonyloxime 2'-O,N-dibenzyloxycarbonyl-N-des-methylerythromycin A 9-benzyloxycarbonyloxime (454 mg) in dry dimethylformamide (3 ml) was treated with 2,6-lutidine (0.24 ml) and chloromethyl methyl ether (0.1 ml) and the mixture stirred at room temperature for 2 h. Employing the same work-up procedure as described in Example 8(a), the title compound was obtained as a colourless foam (212 mg); $\nu_{max}$ (CHCl$_3$) 1730 and 1685 cm$^{-1}$.

(b) 11-O-Methoxymethylerythromycin A 9-oxime

The product fom Example 9(a) (212 mg) was converted into the title compound using a procedure analogous to that described in Example 8(b). The title compound was thus obtained as a colourless foam; $[\alpha]_D^{20}$ −67.2° (1.0% wt/vol in CHCl$_3$); $\nu_{max}$ (CHCl$_3$) 1720 cm$^{-1}$.

EXAMPLE 10

11-O-Ethoxymethylerythromycin A 9-oxime (a)

11-O-Ethoxymethyl-2'-O,N-dibenzyloxycarbonyl-des-N-methylerythromycin A 9-benzyloxycarbonyloxime 2'-O,N-dibenzyloxycarbonyl-des-N-methylerythromycin A 9-benzyloxycarbonyloxime (668 mg) in dry dimethylformamide (4 ml) was treated with 2,6-lutidine (0.28 ml) and chloromethyl ethyl ether (0.14 ml) and the mixture stirred at room temperature for 2 h. Using the work-up procedure described in Example 8(a), the title compound was obtained as a colourless foam (452 mg); $\nu_{max}$ (CHCl$_3$) 1725 and 1690 cm$^{-1}$.

(b) 11-O-Ethoxymethylerythrolycin A 9-oxime

The product from Example 10(a) was converted into the title compound using a procedure analogous to that described in Example 8(b). The title compound was thus obtained as a colourless foam; $[\alpha]D^{20}$ −78.7° (1% wt/vol in EtOH); $\nu_{max}$ (CHCl$_3$) 1720 cm$^{-1}$.

EXAMPLE 11

11-O-[2-Methoxyethoxymethyl]erythromycin A 9-oxime (a)

11-O-[2-Methoxyethoxymethyl]-2'-O,N-dibenzyloxycarbonyl-des-N-methylerythromycin A 9-benzyloxycarbonyloxime 2'-O,N-dibenzyloxycarbonyl-des-N-methylerythromycin A 9-benzyloxycarbonyloxime (668 mg) in dry dimethylformamide (3 ml) was treated with 2,6-lutidine (0.29 ml) and methoxyethoxymethyl chloride (0.20 ml) and the mixture stirred at room temperature for 18 h. Using the work-up procedure described in Example 8(a), the title compound was obtained as a colourless foam (502 mg); $\nu_{max}$ (CHCl$_3$) 1730 and 1695 cm$^{-1}$.

(b) 11-O-[2-methoxyethoxymethyl]erythromycin A 9-oxime

The product from Example 11(a) was converted into the title compound by a procedure analogous to that described in Example 8(b). The title compound was thus obtained as a colourless foam; $[\alpha]_D^{20}$ −74.0° (1% wt/vol in EtOH); $\nu_{max}$ (CHCl$_3$) 1720 cm$^{-1}$;

EXAMPLE 12

11-O-[2-Hydroxyethoxymethyl]erythromycin A 9-oxime (a)

11-O-[2-Hydroxyethoxymethyl]-2'-O,N-dibenzyloxycarbonyl-des-N-methylerythromycin A 9-oxime The product from Example 8(a) (6 g) in methanol (120 ml) was treated with potassium carbonate (1 g) and the mixture stirred at room temperature overnight. Toluene (300 ml) was added and the mixture acidified with citric acid. The methanol was evaporated and the remaining organic solution washed with water. After drying over anhydrous magnesium sulphate, the solvent was evaporated and the residue chromatographed on silica gel using ethyl acetate as eluent to give the title compound as a colourless foam (3.64 g); $\nu_{max}$ (CHCl$_3$) 1725 and 1690 cm$^{-1}$.

(b) 11-O-[2-Hydroxyethoxymethyl]erythromycin A 9-oxime

The product from Example 12(a) was converted into the title compound using a procedure analogous to that described in Example 8(b). The title compound was thus obtained as a colourless foam; $[\alpha]_D^{20}$ −83.2° (1.0% wt/vol in CHCl$_3$); $\nu_{max}$ (CHCl$_3$) 3400 and 1725 cm$^{-1}$; mass spectrum M+822.5102 (C$_{40}$H$_{74}$N hd 2O$_{15}$ requires M 822.5093).

EXAMPLE 13

11-O-[2-N,N-dimethylaminoethoxymethyl]erythromycin A 9-oxime (a)

11-O-[2-Hydroxyethoxymethyl]-2'-O,N-dibenzyloxycarbonyl-des-N-methylerythromycin A 9-acetoxime The product from Example 12(a) (212 mg) in pyridine (3 ml) was treated with acetic anhydride (0.05 ml) and the mixture stirred at room temperature for 1 h. Pyridine was evaporated and the residue dissolved in ethylacetate. The organic solution was washed with citric acid solution and water. After drying over anhydrous magnesium sulphate the solvent was evaporated. Chromatography on silia gel using ethyl acetate as eluent gave the title compound as a colourless foam (165 mg); $[\alpha]_D^{20}$ −104.2° (1.0% wt/vol in EtOH); $\nu_{max}$ (CHCl$_3$) 3450, 1740 and 1690 cm$^{-1}$.

(b)

11-O-[2-Azidoethoxymethyl]-2'-O,N-dibenzyloxycarbonyl-des-N-methylerythromycin A 9-acetoxime 11-O-[2-Hydroxyethoxymethyl]-2'-O,N-dibenzyloxycarbonyl-des-N-methylerythromycin A 9-acetoxime (1.16 g) in tetrahydrofuran (20 ml) was treated with hydrazoic acid (1.8 ml; 1.76 M in toluene) and triphenylphosphine (0.79 g) and the mixture cooled to 0°−5° C. Di-isopropylazidodicarboxylate (0.61 g) was added in one portion and the mixture stirred at room temperature for 1 h. Excess ethyl acetate was added and the organic solution washed with water (×3), saturated aqueous sodium bicarbonate and brine. After drying over anhydrous magnesium sulphate, the solvent was evaporated to give a pale yellow gum. Chromatography on silca gel using ethyl acetate/hexane as eluent gave the title compound as a colourless foam (1.08 g); $[\alpha]_D^{20}$ −83.2° (1.0% wt/vol in CHCl$_3$); $\nu_{max}$ (CHCl$_3$) 2100, 1740 and 1685 cm$^{-1}$.

(c)

11-O-[2-Azidoethoxymethyl]-2'-O,N-dibenzyloxycarbonyl-des-N-methylerythromycin A 9-oxime The product from Example 13(b) (870 mg) in methanol (25 ml) was treated with water (3 ml) and triethylamine (1.25 ml) and the mixture heated at reflux for 2 h. After cooling, the solvent was evaporated and the residue taken up in ethyl acetate (65 ml). The organic extract was washed with water and brine, and dried over anhydrous magnesium sulphate. Evaporation of the solvent and chromatography of the residue on silica gel using ethyl acetate/hexane (1:1) as eluent gave the title compound as a colourless foam (723 mg); $\nu_{max}$ (CHCl$_3$) 1725 and 1685 cm$^{-1}$.

(d) 11-O-[2-N,N-dimethylaminoethoxymethyl]erythromycin A 9-oxime

The product from Example 13(c) was converted into the title compound by a procedure analogous to that described in Example 8(b). The title compound was obtained as a colourless foam; $[\alpha]_D^{20}$ −52.4° (1% wt/vol in EtOH); $\nu_{max}$ (CHCl$_3$) 1720 cm$^{-1}$.

EXAMPLE 14

11-O-[2-(4-Methoxycarbonyl-1,2,3-triazol-1-yl)ethoxymethyl]erythromycin A 9-oxime (a) 11-O-[2-(4-Methoxycarbonyl-1,2,3-triazol-1-yl)ethoxymethyl]-2'-O,N-dibenzyloxycarbonyl-des-N-methyl-erythromycin A 9-oxime The product from Example 13(c) (470 mg) in dry toluene (10 ml) was treated with methyl propiolate (0.1 ml) and the mixture stirred at 45° C. overnight. The reaction mixture was concentrated and chromatographed on silica gel using ethyl acetate/hexane as eluent to give the title compound as a colourless foam (280 mg); $[\alpha]_D^{20}$ −81.5° (1% wt/vol in EtOH); $\nu_{max}$ (CHCl$_3$) 1720 cm$^{-1}$.

(b) 11-O-[2-(4-Methoxycarbonyl-1,2,3-triazol-1-yl)ethoxymethyl]erythromycin A 9-oxime The product from Example 14(a) was converted into the title compound using a procedure analogous to that described in Example 1(b). The title compound was thus obtained as a colourless foam; $[\alpha]_D^{20}$ −80.8° (1.0% wt/vol in CHCl$_3$); $\nu_{max}$ (CHCl$_3$) 1720 cm$^{-1}$.

EXAMPLE 15

11-O-[2-Acetoxyethoxymethyl]erythromycin A 9-oxime (a) 11-O-[2-Acetoxyethoxymethyl]-2'-O,N-dibenzyloxycarbonyl-des-N-methylerythromycin A 9-acetoxime The product from Example 12(a) (3.64 g) in pyridine (20 ml) was cooled to 0°–5° C. and acetic anhydride (0.8 ml; 2 equivalents) added and the mixture stirred at room temperature for 1 h. Pyridine was evaporated and the residue dissolved in ethyl acetate (150 ml). The organic solution was washed with citric acid solution, water and brine. After drying over anhydrous magnesium sulphate, the solvent was evaporated. Chromatography on silica gel using ethyl acetate as eluent gave the title compound as a colourless foam (954 mg); $\nu_{max}$ (CHCl$_3$) 3500, 1730 and 1695 cm$^{-1}$; and a colourless foam (1.5 g) which was identical with the product from Example 13(a).

(b) 11-O-[2-Acetoxyethoxymethyl]-2'-O,N-dibenzyloxycarbonyl-des-N-methylerythromycin A 9-oxime The title compound from Example 15(a) (900 mg) in methanol (10 ml) was treated with potassium carbonate (140 mg) and the mixture stirred at room temperature overnight. The methanol was evaporated and the residue taken up in ethyl acetate. The organic solution was washed with water and the solution dried over anhydrous magnesium sulphate. Evaporation of the solvent and chromatography on silica gel using ethyl acetate/hexane (1:1) as eluent gave the title product as a crisp foam (400 mg); $[\alpha]_D^{20}$ −100.2° (1.0% wt/vol in CHCl$_3$); $\nu_{max}$ (CHCl$_3$) 3500, 1735 and 1695 cm$^{-1}$.

(c) 11-O-[2-Acetoxyethoxymethyl]erythromycin A 9-oxime

The product from Example 15(b) was converted into the title compound by a procedure analogous to that described in Example 1(b). The title compound was thus obtained as a colourless foam; $[\alpha]_D^{20}$ −76.2° (1% wt/vol in EtOH); $\nu_{max}$ (CHCl$_3$) 3450, 1730 and 1695 cm$^{-1}$.

EXAMPLE 16

11-O-[2-Dimethylaminoethoxymethyl]-erythromycin A 9-methoxime (a) 11-O-[2-Azidoethoxymethyl]-2'-O,N-dibenzyloxycarbonyl-des-N-methylerythromycin A 9-methoxime 11-(2-Hydroxyethoxymethyl)-2'-O,N-dibenzyloxycarbonyl-des-N-methylerythromycin A 9-methoxime (200 mg), triphenylphosphine (104 mg) and hydrazoic acid (1.76 M solution in toluene) (344 μl) were dissolved in dry tetrahydrofuran (10 ml). Di-isopropylazodicarboxylate (80 mg) was added and the mixture stirred for 2 hours at ambient temperature. The mixture was diluted with ethyl acetate (50 ml) and washed with water (3×20 ml), saturated aqueous NaHCO$_3$ solution (20 ml), and finally brine (20 ml). The organic layer was dried (MgSO$_4$) and the solvent removed to give an oil which was chromatographed to give the title compound as a colourless foam (145 mg); $\nu_{max}$ (CHCl$_3$) 3545, 2110, 1740 and 1697 cm$^{-1}$; MH$^+$ 1115 m/z (positive ion, thioglycerol, fast atom bombardment spectrum).

(b) 11-O-[2-Dimethylaminoethoxymethyl]erythromycin A 9-methoxime

The product from Example 16(a) was converted into the title compound using a procedure analogous to that described in Example 1(b). The title compound was obtained as a colourless foam; $[\alpha]_D^{20}$ −69.5° (1.0% wt/vol in CHCl$_3$); $\nu_{max}$ (CHCl$_3$) 3500 (br) and 1732 cm$^{-1}$.

EXAMPLE 17

11-O-[N-Methyl-N-formylaminomethyl]erythromycin A 9-oxime (a) 11-O-(N-Methyl-N-formylaminomethyl)-2'-O,N-dibenzyl-oxycarbonyl-des-N-methylerythromycin A 9-benzyloxycarbonyloxime The product from Preparation 2 (568 mg, 0.5 mmol) and 2,6-lutidine (292 μl, 2.5 mmol) were dissolved in dry dimethylformamide (5 ml) and N-methyl-N-formylaminomethyl chloride (160 μl, ca. 1.5 mmol) was added. The mixture was stirred at room temperature for 90 minutes, the solvent removed in vacuo, and the residue partitioned between ethyl acetate and sodium bicarbonate solution. The organic layer was washed with brine and dried over MgSO$_4$. Solvent removal gave the crude material which was chromatographed on silca gel (5 g) using 60% ethyl acetate/hexane as eluant to give the title compound pure (310 mg; 52%) as a colourless foam; $\nu_{max}$ (CHCl$_3$) 3550, 1740, 1680, 700 cm$^{-1}$.

(b)
11-O-[N-Methyl-N-formylaminomethyl]erythromycin A 9-oxime

The product from Example 17(a) (430 mg, 0.35 mmol) was dissolved in a mixture of ethanol (20 ml) and acetate buffer (pH 4.8; 2 ml) and the solution shaken with 10% palladium on charcoal (100 mg) under 1 atmosphere of hydrogen for 45 min. Formaldehyde (2 ml) was added and the hydrogenation continued for a further 2 h. The catalyst was removed by filtration and washed with ethanol. The solvent was removed in vacuo and the residue dissolved in aqueous potassium carbonate and extracted with ethyl acetate (3×50 ml). The organic layer was washed with brine, separated, and dried over MgSO$_4$. Solvent removal gave the crude material which was purified by column chromatography (5 g silica gel, 10% methanol in dichloromethane with 1% conc. ammonia) to give the title compound as a colourless foam (80 mg; 27%); $[\alpha]_D^{20}$ −76.6° (1% wt/vol in CHCl$_3$); $\nu_{max}$ (CHCl$_3$) 3350, 1720, 1675 cm$^{-1}$.

EXAMPLE 18

11-O-[Pyrrolid-2-on-1-ylmethyl]erythromycin A 9-oxime (a)
11-O-[Pyrrolid-2-on-1-ylmethyl]-2'-O,N-dibenzyloxycarbonyl-des-N-methylerythromycin A 9-benzyloxycarbonyloxime The product from Preparation 2 (226 mg, 0.2 mmol) and 2,6-lutidine (116 μl, 1.0 mmol) were dissolved in dry dimethylformamide (5 ml) and N-chloromethylpyrrolid-2-one (80 μl, ca. 0.6 mmol) was added. The mixture was stirred at room temperature for 2 h, the solvent removed in vacuo and the residue partitioned between ethyl acetate and sodium bicarbonate solution. The organic layer was washed with brine and dried over MgSO$_4$. Solvent removal gave the crude material which was chromatographed on silica gel (5 g) using ethyl acetate as elant to give the title compound pure (91 mg, 37%) as a colourless foam; $[\alpha]_D^{20}$ −72.0° (1% wt/vol in CHCl$_3$); $\nu_{max}$ (CHCl$_3$) 3520, 1740, 1690, 700 cm$^{-1}$.

(b) 11-O-[Pyrrolid-2-on-1-ylmethyl]-erythromycin A 9-oxime

The product from Example 18(a) (200 mg, 0.165 mmol) was dissolved in a mixture of ethanol (10 ml) and acetate buffer (pH 4.8, 1 ml) and the solution shaken with 10% palladium on charcoal (50 mg) under 1 atmosphere of hydrogen for 2 h. Formaldehyde (1 ml) was added and the hydrogenation continued for a further 3 h. The catalyst was removed by filtration and washed with ethanol. The solvent was removed in vacuo and the residue dissolved in aqueous potassium carbonate and extracted with ethyl acetate (3×20 ml). The organic layer was washed with brine, separated and dried over MgSO$_4$. Solvent removal gave the crude material which was purified by column chromatography (5 g silica gel, 10% methanol/dichloromethane with 1% conc. ammonia) to give the title compound as a colourless foam (125 mg; 93%); [60 ]$_D^{20}$ −73.2° (C1.0; CHCl$_3$), $\nu_{max}$ (CHCl$_3$) 3400, 1720, 1680 cm$^{-1}$.

EXAMPLE 19

11-O-(2-Acetoxyethyloxymethyl)-erythromycin A 9-O-methoxime (a)
11-O-(2-Acetoxyethyloxymethyl)-2'-O,N-dibenzyloxycarbonyl-des-N-methylerythromycin A 9-O-methoxime 11-O-(2-Hydroxyethyloxymethyl)-2'-O,N-dibenzyloxycarbonyl-des-N-methylerythromycin A 9-O-methoxime (300 mg) in dry pyridine (3 ml) was treated with acetic anhydride (0.056 ml) and the mixture stirred at room temperature for 16 h. The mixture was evaporated to low volume, diluted with ethyl acetate (20 ml) and re-evaporated to give an oil. Chromatography of the residue on silica-gel using ethyl acetate-dichloromethane (2:3) as eluent gave the title compound as a colourless foam (150 mg); $[\alpha]^{20}D$ −73.4° (1.0% wt/vol. in CHCl$_3$) $\nu_{max.}$ (CHCl$_3$) 1735 and 1690 cm$^{-1}$; mass spectrum FAB-MS MH+ 1133 (C$_{58}$H$_{89}$N$_2$O$_{20}$).

(b) 11-O-(2-Acetoxyethyloxymethyl)-erythromycin A 9-O-methoxime

The product from Example 19(a) (150 mg) was dissolved in a mixture of ethanol (10 ml) and acetate buffer (pH 4.8; 1 ml) and the solution shaken with 10% palladium/charcoal (30 mg) under 1 atmosphere of hydrogen for 1 h. 37% Aqueous formaldehyde (1 ml) was added and the hydrogenation continued for a further 1½ h. The catalyst was removed by filtration and washed with ethanol and water. The solvent was removed from the filtrate under reduced pressure and the residue was diluted to about 10 ml with water. The solution was brought to pH 11 with potassium carbonate and extracted with ethyl acetate (3×20 ml). The combined extracts were dried over anhydrous magnesium sulphate and evaporated to give the title compound as a colourless foam (70 mg); $\nu_{max.}$ (CHCl$_3$) 1730 cm$^{-1}$; mass spectrum M+ 878.5361 (C$_{43}$H$_{78}$N$_2$O$_{16}$ requires M 878.5355).

EXAMPLE 20

11-O-(2-Azidoethyloxymethyl)-erythromycin A 9-O-methoxime

11-O-(2-Hydroxyethyloxymethyl)-erythromycin A 9-O-methoxime (263 mg) in dry tetrahydrofuran (12 ml) was treated with triphenylphosphine (248 mg), hydrazoic acid (1.76M solution in toluene; 0.83 ml) and di-isopropylazodicarboxylate (192 mg). The mixture was stirred at room temperature for 15 min. and then diluted with ethyl acetate (50 ml) and washed with saturated aqueous sodium bicarbonate solution (2×20 ml) and brine (20 ml). The ethyl acetate solution was dried over anhydrous magnesium sulphate and evaporated to give a foam. Chromatography of the residue on silica-gel using methanol/chloroform/0.880 ammonia solution (8:92:0.5) as eluent gave the title compound as a colourless foam (197 mg); $[\alpha]^{20}D$ −81.7° (1.0% wt/vol. in CHCl$_3$); $\nu_{max.}$ (CHCl$_3$) 2100, 1725 cm$^{-1}$; mass spectrum M+ 861.5306 (C$_{41}$H$_{75}$N$_5$O$_{14}$ requires M 861.5314).

EXAMPLE 21

11-O-(2-Aminoethyloxynethyl)-erythromycin A 9-O-methoxime

The product from Example 20 (197 mg) was dissolved in a mixture of ethanol (10 ml) and acetate buffer (pH 4.8; 1 ml) and the solution shaken with 10% palladium/charcoal (40 mg) under 1 atmosphere of hydrogen for 1½ h. The catalyst was removed by filtration and washed with ethanol and water. The solvent was removed from the filtrate under redued pressure and the residue was diluted to about 10 ml with water. The solution was brought to pH 11 with potassium carbonate and extracted with ethyl acetate (3×20 ml). The combined extracts were dried over anhydrous magnesium sulphate and evaporated to give a foam. Chromtography of the residue on silca-gel using methanol/chloroform/0.880 ammonia solution (15:85:0.5) as eluent gave the title compound as a colourless foam (85 mg); $[\alpha]^{20}D$ −74.3° (1.0% wt/vol. in CHCl$_3$); $\nu_{max.}$ (CHCl$_3$) 1720 cm$^{-1}$; mass spectrum FAB-MS MH+ 836 (C$_{41}$H$_{78}$N$_3$O$_{14}$).

EXAMPLE 22

11-O-(2-[4-Methoxycarbonyl-1-triazolyl]ethyloxymethyl)erythromycin A 9-O-methoxime (a)

11-O-(2-[4-Methoxycarbonyl-1-triazolyl]ethyloxymethyl)-2′-O,N-dibenzyloxycarbonyl-des-N-methylerythromycin A 9-O-methoxime 11-O-(2-Azidoethyloxymethyl)-2′-O,N-dibenzyloxycarbonyl-des-N-methyl-erythromycin A 9-O-methoxime (300 mg) in dry toluene (6 ml) was treated with methyl propiolate (0.08 ml) and the mixture stirred at 55° for 36 h. The mixture was evaporated to dryness to leave a white foam. Chromatography of the residue on silica-gel using ethyl acetate/hexane (2:1) as eluent gave the title compound as a colourless foam (231 mg); $[\alpha]^{20}D$ −80.3° (1.0% wt/vol. in CHCl$_3$); $\nu_{max.}$ (CHCl$_3$) 1730, 1695 cm$^{-1}$; mass spectrum FAB-MS MH+ 1200 (C$_{60}$H$_{90}$N$_5$O$_{20}$).

(b) 11-O-(2-[4-Methoxycarbonyl-1-triazolyl]ethyloxy methyl)-erythromycin A 9-O-methoxime The product from Example 22(a) (231 mg) was converted into the title compound using a procedure analogous to that described in Example 19(b). The title compound was thus obtained as a colourless foam (152 mg); $[\alpha]^{20}D$ −77.9° (1.0% wt/vol. in CHCl$_3$); $\nu_{max.}$ (CHCl$_3$) 1725 cm$^{-1}$; mass spectrum M+ 945.5545 (C$_{45}$H$_{79}$N$_5$O$_{16}$ requires M 945.5525).

EXAMPLE 23

11-O-(2-[N-Methyl-N-(2-diazo-2-ethyloxycarbonylethyl)]aminoethyloxymethyl)erythromycin A 9-O-methoxime (a)

11-O-(2-[4-Ethyloxycarbonyl-4H-1-triazolinyl]ethyloxymethyl)-2′-O,N-dibenzyloxycarbonyl-des-N-methylerythromycin A 9-O-methoxime 11-O-(2-Azidoethyloxymethyl)-2′-O,N-dibenzyloxycarbonyl-des-N-methylerythromycin A 9-O-methoxime (300 mg) in dry toluene (5 ml) was treated with freshly distilled ethyl acrylate (0.25 ml) and the mixture was stirred at 55° for 3 days. The mixture was evaporated to dryness and the residue was chromatographed on silica-gel using ethyl acetate/hexane (1:1) as eluent to give the title compound as a colourless foam (233 mg); $[\alpha]^{20}D$ −77.6° (1.0% wt/vol. in CHCl$_3$); $\nu_{max.}$ (CHCl$_3$) 1730, 1685 cm$^{-1}$; mass spectrum FAB-MS MH+ 1216 (C$_{61}$H$_{94}$N$_5$O$_{20}$).

(b)

11-O-(2-[N-Methyl-N-(2-diazo-2-ethyloxycarbonylethyl)]aminoethyloxymethyl)erythromycin A 9-O-methoxime The product from Example 23(a) (233 mg) was converted into the title compound using a procedure analogous to that described in Example 19(b). The title compound was thus obtained as a pale yellow foam (65 mg); $[\alpha]^{20}D$ −68.5° (1.0% wt/vol in CHCl$_3$); $\nu_{max.}$ (CHCl$_3$) 2090, 1725, 1675 cm$^{-1}$.

EXAMPLE 24

11-O-(2-Oxoethyloxymethyl)-erythromycin A 9-O-methoxime (a)

11-O-(2-Oxoethyloxymethyl)-2′-O,N-dibenzyloxycarbonyl-des-N-methylerythromycin A 9-O-methoxime 11-O-(2-Hydroxyethyloxymethyl)-2′-O,N-dibenzyloxycarbonyl-des-N-methylerythromycin A 9-O-methoxime (120 mg) in dry toluene (3 ml) was treated with dimethylsulphoxide (0.17 ml), 1-ethyl-3-(3-dimethylaminopropyl)-carbodiimide hydrochloride (64 mg), pyridine (26 mg) and trifluoroacetic acid (6 mg). The mixture was stirred at room temperature for 6 h then diluted with ethyl acetate (50 ml) and washed with water (3×20 ml). The ethyl acetate layer was dried over anhydrous magnesium sulphate and evaporated to give an oil. Chromatography on silica-gel using ethyl acetate/hexane (4:1) as eluent gave the title compound (85 mg); $\nu_{max.}$ (CHCl$_3$) 1730, 1690 cm$^{-1}$; mass spectrum FAB-MS (M-H)+ 1087 (C$_{56}$H$_{83}$N$_2$O$_{19}$).

(b) 11-O-(2-Oxoethyloxymethyl)-erythromycin A 9-O-methoxime

The product from Example 24(a) was converted into the title compound using a procedure analogous to that described in Example 19(b). The title compound was thus obtained as a colourless foam (136 mg); $[\alpha]^{20}D$ −82.4° (1.0% wt/vol. in CHCl$_3$); $\nu_{max}$ (CHCl$_3$) 1725 cm$^{-1}$.

EXAMPLE 25

11-O-Allyloxymethyl-erythromycin A 9-O-methoxime

The product from Example 24(b) (73 mg) in dry tetrahydrofuran (5 ml) was treated dropwise with a solution of methylene triphenylphosphorane in dry tetrahydrofuran until the yellow colour persisted. The mixture was stirred at room temperature for 2 min and then quenched with water (20 ml) and extracted with ethyl acetate (3×20 ml). The combined extracts were washed with water (2×10 ml), brine (10 ml) and dried over anhydrous magnesium sulphate. Evaporation of the solvent gave an oil which was chromatographed on silica-gel using methanol/chloroform/0.880 ammonia (8/92/0.5) as eluent to give the title compound (19 mg); $[\alpha]^{20}D$ −57.6° (1.0% wt/vol. in CHCl$_3$); $\nu_{max.}$ (CHCl$_3$) 1720 cm$^{-1}$; mass spectrum M+ 832.5287 (C$_{42}$H$_{76}$N$_2$O$_{14}$ requires M 832.5300).

EXAMPLE 26

11-O-(3-Methoxycarbonyl-1-propyloxymethyl)-erythromycin A 9-O-methoxime (a)

11-O-(3-Methoxycarbonyl-1-prop-2-enyloxymethyl)-2'-O,N-dibenzyloxycarbonyl-des-N-methylerythromycin A 9-O-methoxime The product from Example 24(a) (150 mg) in dry tetrahydrofuran (5 ml) was treated with carbomethoxymethylene triphenylphosphorane (350 mg). The mixture was stirred at room temperature for 1 h and then evaporated to dryness. Chromatogrpahy on silica-gel using ethyl acetate/hexane (7:3) as eluent gave the title compound as a colourless foam (136 mg); $[\alpha]^{20}D$ −88.5° (1.0% wt/vol. in $CHCl_3$); mass spectrum FAB-MS MH+ 1145 ($C_{59}H_{89}N_2O_{20}$).

(b)

11-O-(3-Methoxycarbonyl-1-propyloxymethyl)erythromycin A 9-O-methoxime

The product from Example 26(a) (114 mg) was converted into the title compound using a procedure analogous to that described in Example 19(b). The title compound was thus obtained as a colourless foam (67 mg); $[\alpha]^{20}D$ −76.6° (1.0% wt/vol in $CHCl_3$); $\nu_{max}$. ($CHCl_3$) 1725 $cm^{-1}$; mass spectrum M+ 892.5517 ($C_{44}H_{80}N_2O_{16}$ requires M 892.5512).

EXAMPLE 27

11-O-(2-N,N-Diethylaminoethyloxymethyl)-erythromycin A 9-O-methoxime

The product from Example 21 (57 mg) was dissolved in a mixture of ethanol (5 ml) and acetate buffer (pH 4.8; 0.5 ml) and acetaldehyde (1 ml) was added. The solution was shaken with 10% palladium/charcoal (30 mg) under 1 atmosphere of hyrogen for 1.75 h. The catalyst was removed by filtration and washed with ethanol and water. The solvent was removed from the filtrate under reduced pressure and the residue was diluted to about 10 ml with water. The solution was brought to pH 11 with potassium carbonate and extracted with ethyl acetate (3×20 ml). The combined extracts were dried over anhydrous magnesium sulphate and evaporated to give the title compound as a white foam (35 mg); $[\alpha]^{20}D$ −76.3° (1.0% wt/vol in $CHCl_3$); $\nu_{max}$. ($CHCl_3$) 1720 $cm^{-1}$; mass spectrum M+ 891.6000 ($C_{45}H_{85}N_3O_{14}$ requires M 891.6036).

EXAMPLE 28

11-O-(2,3-Dihydroxypropyloxymethyl)-erythromycin A 9-O-methoxime (a)

11-O-Allyloxymethyl-2'-O,N-dibenzyloxycarbonyl-des-N-methylerythromycin A 9-O-methoxime The product from Example 24(a) (452 mg) in dry tetrahydrofuran (25 ml) was treated dropwise with a solution of methylene triphenylphosphorane in dry tetrahydrofuran until the yellow colour persisted. The mixture was stirred at room temperature for 5 min, quenched with water (100 ml) and then extracted with ethyl acetate (3×100 ml). The combined extracts were dried over anhydrous magnesium sulphate and evaorated to give an oil. Chromatography on silica-gel using ethyl acetate/hexane (2:3) as eluent gave the title compound as a colourless foam (245 mg); $^{13}C$ NMR ($CDCl_3$) δ (inter alia) 137.17, 116.21.

(b)

11-O-(2,3-Dihydroxypropyloxymethyl)-2'-O,N-dibenzyloxycarbonyl-des-N-methylerythromycin A 9-O-methoxime The product from Example 28(a) (162 mg) in diethyl ether (5 ml) was treated with osmium tetroxide (45 mg) and pyridine (2 ml). The mixture was stirred at room temperature for 16 h and the solvent removed under reduced pressure. The brown residue was taken up in pyridine (5 ml) and treated with aqueous sodium hydrogen sulphite solution (45% wt/vol; 3 ml). The mixture was stirred vigorously for 2½ h and tetrahydrofuran (3 ml) added to make the solution homogeneous. The mixture was then diluted with ethyl acetate (50 ml), washed with water (2×20 ml) and dried over anhydrous magnesium sulphate. Evaporation of the solvent gave the title compound as white foam (139 mg); $[\alpha]^{20}D$ −78.9° (1.0% wt/vol. in $CHCl_3$); $\nu_{max}$. ($CHCl_3$) 1740, 1690 $cm^{-1}$; mass spectrum FAB-MS MH+ 1121 ($C_{57}H_{89}N_2O_{20}$).

(c)

11-O-(2,3-Dihydroxypropyloxymethyl)-erythromycin A 9-O-methoxime

The product from Example 28(b) (139 mg) was converted into the title compound using a procedure analogous to that described in Example 19(b). The title compound was thus obtained as a colourless foam (53 mg); $[\alpha]^{20}D$ −82.8° (1.0% wt/vol. in $CHCl_3$); $\nu_{max}$. ($CHCl_3$) 3440, 1720 $cm^{-1}$; mass spectrum M+ 866.5340 ($C_{42}H_{78}N_2O_{16}$ requires M 866.5355).

EXAMPLE 29

11-O-Carboxymethyloxymethyl-erythromycin A 9-O-methoxime (a)

11-O-Carboxymethyloxymethyl-2'-O,N-dibenzyloxycarbonyl-des-N-methylerythromycin A 9-O-methoxime The product from Example 24(a) (200 mg) in tetrahydrofuran (12 ml) was treated with sodium bicarbonate (17 mg) in water (6 ml) and the solution was stirred with 5% palladium/charcoal (300 mg) while oxygen was bubbled through for 2 h at 50° and a further 1 h at room temperature. The catalyst was removed by filtration and washed with tetrahydrofuran and water. The filtrate was evaporated to low volume, diluted with water (10 ml) and acidified with citric acid. The 3 solution was extracted with ethyl acetate (3×20 ml) and the combined extracts dried over anhydrous magnesium sulphate. Evaporation of the solvent gave the title compound as a colourless foam (168 mg); $[\alpha]^{20}D$ −68.9° (1.0% wt/vol. in $CHCl_3$); $\nu_{max}$. ($CHCl_3$) 1735, 1685 $cm^{-1}$; mass spectrum FAB-MS (M-H)+ 1103 ($C_{56}H_{83}N_2O_{20}$).

(b) 11-O-Carboxymethyloxymethyl-erythromycin A 9-O-methoxime

The product from Example 29(a) (168 mg) was dissolved in a mixture of ethanol (10 ml) and acetate buffer (pH 4.8; 1 ml) and the solution shaken with 10% palladium/charcoal (40 mg) under 1 atmosphere of hydrogen for 1 h. 37% Aqueous formaldehyde (1 ml) was added and the hydrogenation continued for a further 1½ h. The catalyst was removed by filtration and washed with ethanol and water. The solvent was removed from the filtrate under reduced pressure and the residue was taken up in toluene (3×20 ml) and evaporated to dryness again. The residue was chromatographed on silanised silica-gel using methanol/phosphate buffer (pH 7.0) (3:2) as eluent. The title compound was obtained free of buffer by triturating the residue of the combined and evaporated column fractions with ethanol (3×10 ml), filtering and evaporating the filtrate. Thus the title compound was obtained as a colourless foam (78 mg); $[\alpha]^{20}D$ −64.0° (1.0% wt/vol. in $CHCl_3$); $\nu_{max.}$ ($CHCl_3$) 1725, 1600 $cm^{-1}$; mass spectrum FAB-MS (3-nitrobenzyl alcohol matrix+sodium acetate) $(M-H+2Na)^+$ 895 ($C_{41}H_{73}N_2O_{16}Na_2$).

EXAMPLE 30

11-O-(3-Benzoyloxypropyloxymethyl)-erythromycin A 9-O-methoxime (a)

11-O-(3-Benzoyloxypropyloxymathyl)-2'-O,N-dibenzyloxycarbonyl-des-N-methylerythromycin A 9-O-methoxime 2'-O,N-Dibenzyloxycarbonyl-des-N-methylerythromycin A 9-O-methoxime (3.19 g) in dry dimethylformamide (24 ml) was treated with 2,6-lutidine (1.8 ml) and 3-benzoyloxypropyloxymethyl chloride (2.15 g). The mixture was stirred at room temperature for 16 h, diluted with ethyl acetate (100 ml), washed with water (3×50 ml) and dried over anhydrous magnesium sulphate. Evaporation of the solvent gave an oil which was chromatographed on silica-gel using ethyl acetate/dichloromethane (2:3) as eluent to give the title compound as a colourless foam (3.17 g); $[\alpha]^{20}D$ −90.6° (1.0% wt/vol in $CHCl_3$); $\nu_{max.}$ ($CHCl_3$) 1718 (broad); mass spectrum FAB-MS (3-nitrobenzyl alcohol matrix+sodium acetate) $MNa^+$ 1231 ($C_{64}H_{92}N_2O_{20}Na$).

(b)

11-O-(3-Benzoyloxypropyloxymethyl)-erythromycin A 9-O-methoxime

The product from Example 30(a) (250 mg) was converted into the title compound using a procedure analogous to that described in Example 19(b). The title compound was thus obtained as a colourless foam (143 mg); $[\alpha]^{20}D$ −75.5° (1.0% wt/vol. in $CHCl_3$); $\nu_{max.}$ ($CHCl_3$) 1710 $cm^{-1}$; mass spectrum $M^+$ 954.5621 ($C_{49}H_{82}N_2O_{16}$ requires M 954.5664).

EXAMPLE 31

11-O-(3-Hydroxypropyloxymethyl)-erythromycin A 9-O-methoxime (a)

11-O-(3-Hydroxypropyloxymethyl)-2'-O,N-dibenzyloxycarbonyl-des-N-methylerythromycin A 9-O-methoxime The product from Example 30(a) (2.83 g) in methanol (75 ml) was treated with potassium carbonate (164 mg) and the mixture stirred at room temperature for 16 h. The mixture was acidified with an aqueous solution of citric acid, diluted with toluene (100 ml) and evaporated to low volume. The residue was diluted to 100 ml with toluene, washed with water (3×50 ml) then brine (50 ml), dried over anhydrous magnesium sulphate and evaporated to give an oil. Chromatography on silica-gel using ethyl acetate/dichloromethane (3:2) as 9 eluent gave the title compound as a colourless foam (1.55 g); $[\alpha]^{20}D$ −90.3° (1.0% wt/vol. in $CHCl_3$); $\nu_{max.}$ ($CHCl_3$) 1735, 1685 $cm^{-1}$; mass spectrum FAB-MS (3-nitrobenzyl alcohol matrix+sodium acetate) $MNa^+$ 1127 ($C_{57}H_{88}N_2O_{19}Na$).

(b) 11-O-(3-Hydroxypropyloxymethyl)-erythromycin A 9-O-methoxime

The product from Example 31(a) (250 mg) was converted into the title compound using a procedure analogous to that described in Example 19(b). The title compound was thus obtained as a colourless foam (180 mg); $[\alpha]^{20}D$ −84.4° (1.0% wt/vol. in $CHCl_3$); $\nu_{max.}$ ($CHCl_3$) 3500, 1720 $cm^{-1}$; mass spectrum $M^+$ 850.5365 ($C_{42}H_{78}N_2O_{15}$ requires M 850.5401).

EXAMPLE 32

11-O-(3-Dimethylaminopropyloxymethyl)-erythromycin A 9-O-methoxime (a)

11-O-(3-Azidopropyloxymethyl)-2'-O,N-dibenzyloxycarbonyl-des-N-methylerythromycin A 9-O-methoxime The product from Example 31(a) (600 mg) in dry tetrahydrofuran (30 ml) was treated with triphenylphosphine (624 mg), hydrazoic acid (1.76M solution in toluene; 2.0 ml) and diisopropylazodicarboxylate (480 mg). The mixture was stirred at room temperature for 15 min, diluted with ethyl acetate (150 ml) and washed with saturated aqueous sodium bicarbonate solution (50 ml) and brine (50 ml). The organic layer was dried over anhydrous magnesium sulphate and evaporated to give a foam. Chromatography on silica-gel using diethyl ether/hexane (1:1) followed by ethyl acetate/hexane (2:1) as eluent gave the title compound as a colourless foam (552 mg); $[\alpha]^{20}D$ −92.1° (1.0% wt/vol. in $CHCl_3$); $\nu_{max.}$ ($CHCl_3$) 2100, 1730, 1690 $cm^{-1}$; mass spectrum FAB-MS (3-nitrobenzyl alcohol matrix+sodium acetate) $MNa^+$ 1152 ($C_{57}H_{87}N_5O_{18}Na$).

(b)

11-O-(3-Dimethylaminopropyloxymethyl)-erythromycin A 9-O-methoxime

The product from Example 32(a) (552 mg) was dissolved in a mixture of ethanol (26 ml) and acetate buffer (pH 4.8; 2.6 ml) and the solution shaken with 10% palladium/charcoal (132 mg) under 1 atmosphere of hydrogen for 1 h. 37% Aqueous formaldehyde (2 ml) was added and the hydrogenation continued for a further 1½ h. The catalyst was removed by filtration and washed with ethanol and water. The solvent was removed from the filtrate under reduced pressure and the residue was diluted with acetate buffer (10 ml) and washed with ethyl acetate (3×10 ml). The combined washings were discarded. The aqueous layer was brought to pH 11 with potassium carbonate and extracted with ethyl acetate (3×20 ml). The combined extracts were dried over anhydrous magnesium sulphate and evaporated to give the title compound as a colourless foam (259 mg); $[\alpha]^{20}D$ −77.0° (1.0% wt. vol. in $CHCl_3$); $\nu_{max.}$ ($CHCl_3$) 1725 $cm^{-1}$; mass spectrum $M^+$ 877.5853 ($C_{44}H_{83}N_3O_{14}$ requires M 877.5875).

EXAMPLE 33

11-O-(3-Acetoxypropyloxymethyl)-erythromycin A 9-O-methoxime (a)

11-O-(3-Acetoxypropyloxymethyl)-2'-O,N-dibenzyloxycarbonyl-des-N-methylerythromycin A 9-O-methoxime The product from Example 31(a) (500 mg) in dry pyridine (5 ml) was treated with acetic anhydride (0.5 ml) and the mixture stirred at room temperature for 16 h. The mixture was diluted with water (20 ml) and extracted with ethyl acetate (3×50 ml). The combined extracts were dried over anhydrous magnesium sulphate and evaporated to give an oil. Chromatogrpahy on silicagel using ethyl acetate/dichloromethane (2:3) as eluent gave the title compound as a colourless foam (390 mg); $[\alpha]^{20}D$ −85.1° (1.0% wt. vol in CHCl$_3$); $\nu_{max}$. (CHCl$_3$) 1730, 1690 cm$^{-1}$; mass spectrum FAB-MS (3-nitrobenzyl alcohol matrix+sodium acetate) MNa$^+$ 1169 (C$_{59}$H$_{90}$N$_2$O$_{20}$Na).

(b) 11-O-(3-Acetoxypropyloxymethyl)-erythromycin A 9-O-methoxime

The product from Example 33(a) (378 mg) was converted into the title compound using a procedure analogous to that described in Example 19(b). The title compound was thus obtained as a colourless foam (265 mg); $[\alpha]^{20}D$ −82.4° (1.0% wt/vol in CHCl$_3$); $\nu_{max}$. (CHCl$_3$) 1725 cm$^{-1}$; mass spectrum M$^+$ 892.5480 (C$_{44}$H$_{80}$N$_2$O$_{16}$ requires M 892.5507).

EXAMPLE 34

11-O-(2-(Piperidin-1-yl)-ethyloxymethyl)-erythromycin A 9-O-methoxime (a)

11-O-(2-Bromoethyloxymethyl)-2'-O,N-dibenzyloxycarbonyl-des-N-methylerythromycin A 9-O-methoxime 2'-O,N-Dibenzyloxycarbonyl-des-N-methylerythromycin A 9-O-methoxime (700 mg) in dry dimethylformamide (6 ml) was treated with 2,6-lutidine (0.8 ml) and 2-bromoethyloxymethyl chloride (0.875 ml). The mixture was stirred at room temperature for 6 h, diluted with ethyl acetate (50 ml) and washed with water (3×20 ml). The solution was dried over anhydrous magnesium sulphate and evaporated to give an oil. Chromatography on silica-gel using ethyl acetate/dichloromethane (1:4) and then (3:7) as eluent gave the title compound as a colourless foam (565 mg); $[\alpha]^{20}D$ −82.4° (1.0% wt/vol. in CHCl$_3$); $\nu_{max}$. (CHCl$_3$) 1735, 1695 cm$^{-1}$; mass spectrum FAB-MS (3-nitrobenzyl alcohol matrix+sodium acetate) MNa$^+$ 1175 (C$_{56}$H$_{85}$BrN$_2$O$_{18}$Na).

(b)

11-O-(2-Piperidin-1-yl)-ethyloxymethyl)-2'-O,N-dibenzyloxycarbonyl-des-N-methylerythromycin A 9-O-methoxime The product from Example 34(a) (300 mg) in dry dimethylformamide (5 ml) was treated with piperidine (200 mg) and the mixture stirred at 65° for 5 h. The mixture was diluted with water (50 ml) and extracted with ethyl acetate (3×50 ml). The combined extracts were dried over anhydrous magnesium sulphate and evaporated to give a foam. Chromatography on silica-gel uing methanol/chloroform/0.880 ammonia (7:93:0.5) as eluent gave the title compound as a colourless foam (228 mg); $[\alpha]^{20}D$ −82.1° (c, 1.0% wt/vol. in CHCl$_3$); $\nu_{max}$. (CHCl$_3$) 1735, 1690 cm$^{-1}$; mass spectrum FAB-MS (3-nitrobenzyl alcohol+sodium acetate) MNa$^+$ 1180 (C$_{61}$H$_{95}$N$_3$O$_{18}$Na).

(c)

11-O-(2-Piperidin-1-yl)-ethyloxymethyl)erythromycin A 9-O-methoxime

The product from Example 34(b) (214 mg) was converted into the title compound using a procedure analogous to that described in Example 19(b). The title compound was thus obtained as a colourless foam (121 mg); $[\alpha]^{20}D$ −72.0° (1.0% wt/vol. in CHCl$_3$); $\nu_{max}$. (CHCl$_3$) 1725 cm$^{-1}$; mass spectrum FAB-MS MH$^+$ 904 (C$_{46}$H$_{86}$N$_3$O$_{14}$).

EXAMPLE 35

11-O-[(2-N-methyl,2-N-ethylamino)ethoxymethyl]erythromycin A 9-O-methoxime (a)

11-O-(2-N-Ethylaminoethyloxymethyl)-2'-O,N-dibenzyloxycarbonyl-des-N-methylerythromycin A 9-O-methoxime The product from Example 34(a) (250 mg) was dissolved in ethylamine (2 ml) and the solution placed in a sealed tube. The mixture was heated to 65° for 4 h, then diluted with water (20 ml) and extracted with ethyl acetate (3×50 ml). The combined extracts were dried over anhydrous magnesium sulphate and evaporated to give a foam. Chromatography on silica-gel using methanol/chloroform/0.880 ammonia solution (8:92:0.5) as eluent gave the title compound as a colourless foam (175 mg); $[\alpha]^{20}D$ −85.3° (1.0% wt/vol. in CHCl$_3$); $\nu_{max}$. (CHCl$_3$) 3450, 1735, 1660 (broad) cm$^{-1}$; mass spectrum FAB-MS (3-nitrobenzyl alcohol matrix+sodium acetate) MNa$^+$ 1140 (C$_{58}$H$_{91}$N$_3$O$_{18}$Na).

(b)

11-O-[(2-N-methyl1,2-N-ethylamino)ethoxymethyl)erythromycin A 9-O-methoxime

The product from Example 35(a) (149 mg) was converted into the title compound by a procedure analogous to that described in Example 19(b). The title compound was obtained as a colourless foam (106 mg); $[\alpha]^{20}D$ −73.6° (1.0% wt/vol. in CHCl$_3$); $\nu_{max}$. (CHCl$_3$) 1720 cm$^{-1}$; mass spectrum FAB-MS MH$^+$ 878 (C$_{44}$H$_{84}$N$_3$O$_{14}$).

EXAMPLE 36

11-O-(2-Phenyloxyethyloxymethyl)-erythromycin A 9-O-methoxime (a)

11-O-(2-Phenyloxyethyloxymethyl)-2'-O,N-dibenzyloxycarbonyl-des-N-methylerythromycin A 9-O-methoxime 2'-O,N-Dibenzyloxycarbonyl-des-N-methylerythromycin A 9-O-methoxime (300 mg) in dry dimethylformamide (3 ml) was treated with 2,6-lutidine (0.571 ml) and 2-phenyloxyethyloxymethyl chloride (0.588 ml). The mixture was stirred at room temperature for 6 h, diluted with ethyl acetate (100 ml) and washed with water (3×20 ml). The ethyl acetate fraction was dried over anhydrous magnesium sulphate and evaporated to give a foam. Chromatography on silica-gel using ethyl acetate/dichloromethane (2:3) followed by repeat chromatography on silica-gel using ethyl acetate/hexane (1:1) as eluents gave the title compound as a colourles foam (128 mg); $[\alpha]^{20}D$ −83.2° (1.0% wt/vol. in CHCl$_3$); $\nu_{max.}$(CHCl$_3$) 1740, 1688 cm$^{-1}$; mass spectrum FAB-MS (3-nitrobenzyl alcohol matrix+sodium acetate) MNa+ 1189 (C$_{62}$H$_{90}$N$_2$O$_{19}$Na).

(b) 11-O-(2-Phenyloxyethyloxymethyl)-erythromycin A 9-O-methoxime

The product from Example 36(a) (116 mg) was converted into the title compound by a procedure analogous to that described in Example 19(b). The title compound was obtained as a colourless foam (83 mg); $[\alpha]^{20}D$ −73.2° (1.0% wt/vol. in CHCL$_3$); $\nu_{max.}$ (CHCl$_3$) 1725 cm$^{-1}$; mass spectrum FAB-MS MH+ 913 (C$_{47}$H$_{81}$N$_2$O$_{15}$).

EXAMPLE 37

11-O-(2-N,N-dimethylaminoethyloxymethyl)-erythromycin A 9-O-methoxime (a) 11-O-(2-N,N-dimethylaminoethyloxmethyl)-2'-O,N-dibenzyloxycarbonyl-des-N-methylerythromycin A 9-O-methoxime The product from Example 34(a) (256 mg) in dry dimethylformamide (10 ml) was treated with excess dimethylamine gas for 10 min at room temperature and for 2 h at 60°. The mixture was diluted with water (50 ml), brought to pH 11 with solid potassium carbonate and extracted with ethyl acetate (3×100 ml). The combined extracts were dried over anhydrous magnesium sulphate and evaporated to give a foam. Chromatography on silica-gel using methanol/chloroform/0.880 ammonia (8:92:0.5) as eluent gave the title compound as a colourless foam (176 mg); $[\alpha]^{20}D$ −81.2° (1.0% wt/vol. in CHCl$_3$); $\nu_{max.}$ (CHCl$_3$) 1735 (broad), 1685 cm$^{-1}$; mass spectrum FAB-MS (3-nitrobenzyl alcohol matrix+sodium acetate) MNa+ 1140 (C$_{58}$H$_{91}$N$_3$O$_{18}$Na).

(b) 11-O-(2-N,N-dimethylaminoethyloxymethyl)erythromycin A 9-O-methoxime

The product from Example 37(a) (160 mg) was dissolved in a mixture of ethanol (7 ml) and acetate buffer (pH 4.8; 0.7 ml) and the solution shaken with 10% palladium/charcoal (40 mg) under 1 atmosphere of hydrogen for 1 h. 37% Aqueous formaldehyde (1 ml) was added and the hyrogenation continued for a further 1½ h. The catalyst was removed by filtration and washed with ethanol and water. The filtrate was evaporated to low volume and the residue was taken up in acetate buffer (pH 4.8; 5 ml) and washed with ethyl acetate (3×5 ml). The ethyl acetate washings were discarded, the aqueous solution was brought to pH 11 with potassium carbonate and the solution extracted with ethyl acetate (3×20 ml). The combined extracts were dried over anhydrous magnesium sulphate and then evaporated to give the title compound as a colourless foam (110 mg). Recrystallisation of the product from ethyl acetate/hexane gave the title compound as a crystalline solid; $[\alpha]^{20}D$ −69.5° (1.0% wt/vol. in CHCl$_3$); $\nu_{max.}$ (CHCl$_3$) 3500 (broad), 1732 cm$^{-1}$; m.p. 216°–218° C.; (Found: C, 60.00%; H, 9.55%; N, 4.52%; C$_{43}$H$_{81}$N$_3$O$_{14}$ requires C, 59.77%; H, 9.45% and N, 4.86%); mass spectrum FAB-MS MH+ 864 (C$_{43}$H$_{82}$N$_3$O$_{14}$).

EXAMPLE 38

11-O-[N-Methyl-N-acetylaminomethyl]erythromycin A 9-oxime (a) 11-O-[N-Methyl-N-acetylaminomethyl]-2'-O,N-dibenzyloxycarbonyl-des-N-methylerythromycin A 9-benzyloxycarbonyloxime The product from Preparation 2 (1.14 g, 1.0 mmol) and 2,6-lutidine (0.59 ml, 5.0 mmol) were dissolved in dry 2 dimethylformamide (10 ml) and N-methyl-N-acetylaminomethyl chloride (350 μl, ca. 3.0 mmol) was added. The mixture was stirred at room temperature for 90 minutes, the solvent removed in vacuo, and the residue partitioned between ethyl acetate and sodium bicarbonate solution. The organic layer was washed with brine and dried over MgSO$_4$. Solvent removal gave crude material (1.3 g) which was chromatographed on silica gel (25 g, 60–70% ethyl acetate/hexane as eluent) to give the title compound (530 mg, 43%) as a colourless foam; $[\alpha]^{20}D$ −79.3° (1% wt/vol., CHCl$_3$); $\nu_{max.}$ (CHCl$_3$) 3450, 1740, 1690, 1650, 690 cm$^{-1}$.

(b) 11-O-[N-Methyl-N-acetylaminomethyl]-erythromycin A 9-oxime

The product from Example 38(a) (530 mg, 0.43 mmol) was dissolved in a mixture of ethanol (20 ml) and acetate buffer (pH 4.8; 2 ml) and the solution shaken with 10% palladium on charcoal (100 mg) under 1 atmosphere of hydrogen for 45 minutes. Formaldehyde (2 ml) was added and the hydrogenation continued for a further 2 h. The catalyst was removed by filtration and washed with ethanol. The solvent was removed in vacuo and the residue dissolved in aqueous potassium carbonate and extracted with ethyl acetate (3×50 ml). The organic layer was washed with brine, separated and dried over MgSO$_4$. Solvent removal gave the title compound as a colourless foam (320 mg; 89%); $[\alpha]^{20}D$ −70.2° (1% wt/vol., CHCl$_3$); $\nu_{max.}$ (CHCl$_3$), 3400, 1725, 1640 cm$^{-1}$; M+ 833.5242 (C$_{41}$H$_{75}$N$_3$O$_{14}$ requires M 833.5252).

EXAMPLE 39

11-O-(N-Methoxycarbonyl-N-methylaminomethyl)erythromycin A 9-oxime (a) 11-O-[N-Methoxycarbonyl-N-methylaminomethyl]-2'-O,N-dibenzyloxycarbonyl-des-N-methylerythromycin A 9-benzyloxycarbonyloxime The product from Preparation 2 (2.28 g, 2.0 mmol) and 2,6-lutidine (1.18 ml, 10 mmol) were dissolved in dry dimethylformamide (20 ml) and N-methyl-N-methoxycarbonylaminomethyl chloride (824 mgs, 6.0 mmol) was added. The mixture was stirred at room temperature for 3 h, the solvent removed in vacuo, and the residue partitioned between ethyl acetate and sodium bicarbonate solution. The organic layer was washed with brine and dried over MgSO$_4$. Solvent removal gave the crude material which was chromatographed on silica gel using 70% ethyl acetate/hexane as eluent to give the title compound (1.03 g, 42%); $\nu_{max.}$ (CHCl$_3$), 3500, 1700, 690 cm$^{-1}$; $[\alpha]^{20}D$ −67.6° (1% wt/vol., CHCl$_3$).

(b)

11-O-[N-methoxycarbonyl-N-methylaminomethyl]erythromycin A 9-oxime

The product from Example 39(a) (1.03 g, 0.83 mmol) was dissolved in ethanol (20 ml) and acetate buffer (pH 4.8, 2 ml) and the solution shaken with 10% palladium on charcoal (250 mg) under 1 atmosphere of hydrogen for 30 minutes. Formaldehyde (2 ml) was added and the hydrogenation continued for a further 2 h. The catalyst was removed by filtration and washed with ethanol. The solvent was removed in vacuo and the residue dissolved in aqeuous potassium carbonate and extracted with ethyl acetate (3×50 ml). The organic layer was washed with brine, separated, and dried over $MgSO_4$. Solvent removal gave the crude material which was purified by column chromatography on silica (10% methanol in dichloromethane with 1% conc. ammonia) to give the title compound as a colourless foam (240 mgs, 29%); $[\alpha]^{20}D$ −60.7 (1% wt/vol., $CHCl_3$); 3450, 1700 cm$^{-1}$; mass spectrum M+ 849.5206 ($C_{41}H_{75}N_3O_{15}$ requires M 849.5202); (Found: C, 58.03%; H, 9.08%, N, 4.68%. $C_{41}H_{75}N_3O_{15}$ requires C, 57.95%; H, 8.83%; N, 4.95%).

EXAMPLE 40

11-O-(N-Ethoxycarbonyl-N-methylaminomethyl)erythromycin A 9-oxime (a)

11-O-(N-Ethoxycarbonyl-N-methylaminomethyl)-2'-O,N-dibenzyloxycarbonyl-des-N-methylerythromycin A 9-benzyloxycarbonyloxime The product from Preparation 2 (568 mg, 0.5 mmol) and 2,6-lutidine (292 μl, 2.5 mmol) were dissolved in dry dimethylformamide (5 ml) and N-methoxycarbonyl-N-methylaminomethyl chloride (228 mg), 1.5 mmol) was added. The mixture was stirred at room temperature for 2 h, the solvent removed in vacuo and the residue partitioned between ethyl acetate and sodium bicarbonate solution. The organic layer was washed with brine and dried over $MgSO_4$. Solvent removal gave the crude material.

(b)

11-O-(N-Ethoxycarbonyl-N-methylaminomethyl)erythromycin A 9-oxime

The crude product from Example 40(a) was dissolved in a mixture of ethanol (20 ml) and acetate buffer (pH 4.8; 2 ml) and the solution shaken with 10% palladium on charcoal (200 mg) under 1 atmosphere of hydrogen for 30 minutes. Formaldehyde (2 ml) was added and the hydrogenation continued for a further 1 h. The catalyst was removed by filtration and washed with ethanol. The solvent was removed in vacuo and the residue dissolved in aqueous potassium carbonate and extracted with ethyl acetate (3×50 ml). The organic layer was washed with brine, separated, and dried over $MgSO_4$. Solvent removal gave the crude material as an oil which was purified by column chromatography on silanised silica using 50% methanol in pH 7 phosphate buffer as eluent to give the title compound (71 mg, ($CHCl_3$); 3400, 1720, 1690 cm$^{-1}$; mass spectrum M+ 863.5351 ($C_{42}H_{77}N_3O_{15}$ requires M 863.5358).

EXAMPLE 41

11-O-(N-Phenylsulphonyl-N-methylaminomethyl)erythromycin A 9-oxime (a)

11-O-(N-Phenylsulphonyl-N-methylaminomethyl)-2'-O,N-dibenzyloxycarbonyl-des-N-methylerythromycin A 9-benzyloxycarbonyloxime The product from Preparation 2 (568 mg, 0.5 mmol) and 2,6-lutidine (292 μl, 2.5 mmol) were dissolved in dry dimethylformamide (5 ml) and N-methyl-N-phenylsulphonylaminomethyl chloride (329 mg, 1.5 mmol) was added. The mixture was stirred at room temperature overnight, the solvent removed in vacuo, and the residue partitioned between ethyl acetate and water. The organic layer was washed with brine and dried over magnesium sulphate. Solvent removal gave the crude material which was chromatographed on silica-gel using 2–3% methanol in dichloromethane as eluent to give the title compound (183 mg, 28%); $[\alpha]^{20}D$ −71.7° (1% wt/vol., $CHCl_3$); $v_{max}$. ($CHCl_3$), 3500, 1740, 1690, 1340, 1160, 690 cm$^{-1}$.

(b)

11-O-(N-Phenylsulphonyl-N-methylaminomethyl)erythromycin A 9-oxime

The product from Example 41(a) (179 mg, 0.14 mmol) was dissolved in a mixture of ethanol (20 ml) and acetate buffer (pH 4.8; 2 ml) and the solution shaken with 10% palladium on charcoal (60 mg) under 1 atmosphere of hydrogen for 45 minutes. Formaldehyde (2 ml) was added and the hydrogenation continued for a further 2 h. The catalyst was removed by filtration and washed with ethanol. The solvent was removed in vacuo and the residue dissolved in aqueous potassium carbonate and extracted with ethyl acetate. The organic layer was washed with brine, separated, and dried over $MgSO_4$. Solvent removal gave the title compound (90 mg, 69%); $[\alpha]^{20}D$ −68.1° (1% wt/vol., $CHCl_3$), $v_{max}$. $CHCl_3$) 3500, 1720, 1340, 1160 cm$^{-1}$.

EXAMPLE 42

11-O-(N-Methanesulphonyl-N-methylaminomethyl)erythromycin A 9-oxime (a)

11-O-(N-Methanesulphonyl-N-methylaminomethyl)-2'-O,N-dibenzyloxycarbonyl-des-N-methyl erythromycin A 9-benzyloxycarbonyloxime The product from Preparation 2 (1.14 g, 1.0 mmol) and 2,6-lutidine (590 μl, 5.0 mmol) were dissolved in dry dimethyl-formamide (10 ml) and N-methyl-N-methylsulphonylaminomethyl chloride (0.50 g, 3.0 mmol). The mixture was stirred at room temperature for 3 h, the solvent removed in vacuo, and the residue partitioned between ethyl acetate and water. The organic layer was washed with brine and dried over $MgSO_4$. Solvent removal gave the crude material (1.5 g) which was chromatographed on silica gel (50 g) using 3% methanol in dichloromethane as eluent to give the title compound (790 mg, 63%); $[\alpha]^{20}D$ −88.0° (1% wt/vol., $CHCl_3$); $v_{max}$.($CHCl_3$), 3500, 1740, 1690, 1330, 1165, 690 cm$^{-1}$; mass spectrum (3-nitrobenzyl alcohol matrix+sodium acetate) MNa+ 1280 ($C_{63}H_{91}N_3O_{21}Na$).

(b)
11-O-(N-Methanesulphonyl-N-methylaminomethyl-)erythromycin A 9-oxime

The product from Example 42(a) (790 mgs, 0.63 mmol) was dissolved in a mixture of ethanol (50 ml) and acetate buffer (pH 4.8; 5 ml) and the solution shaken with 10% palladium on charcoal (200 mg) under 1 atmosphere of hydrogen for 45 minutes. Formaldehyde (5 ml) was added and the hydrogenation continued for a further 2 h. The catalyst was removed by filtration and washed with ethanol. The solvent was removed in vacuo and the residue dissolved in aqueous potassium carbonate and extracted with ethyl acetate (3×50 ml). The organic layer was washed with brine, separated, and dried over $MgSO_4$. Solvent removal gave crude material which was purified by column chromatography (30 g silica gel, 7% methanol in dichloromethane with 1% conc. ammonia) to give the title compound (330 mg, 60%); $[\alpha]^{20}D$ −82.9° (1% wt/vol., $CHCl_3$); $\nu_{max}$. ($CHCl_3$), 3530, 1720, 1330, 1150 cm$^{-1}$; mass spectrum FAB-MS (3-nitrobenzyl alcohol matrix+sodium acetate) $MNa^+$ 892 ($C_{40}H_{75}N_3O_{15}SNa$).

EXAMPLE 43

11-O-[2-Methanesulphonyloxyethoxymethyl]erythromycin A 9-oxime (a)
11-O-[2-Methanesulphonyloxyethoxymethyl]-2'-O,N-dibenzyloxycarbonyl-des-N-methylerythromycin A 9-acetoxime The product from Example 13(a) (200 mg) in dry pyridine (3 ml) was treated with methanesulphonyl chloride (0.02 ml) at 0°–5° and the mixture stirred at room temperature for 1 h. The pyridine was evaporated and the residue partitioned between ethyl acetate and water. Organic solution was washed with aqueous citric acid solution, aqueous sodium bicarbonate solution and finally brine. After drying over anhydrous magnesium sulphate the solvent was evaporated. Chromatography of the residue on silica-gel using ethyl acetate-hexane as eluent gave the title product as a colourless foam (110 mg), $[\alpha]^{20}D$ −100.2° (c 1.0% in $CHCl_3$); $\nu_{max}$. ($CHCl_3$) 1740 and 1690 cm$^{-1}$.

(b)
11-O-[2-Methanesulphonyloxyethoxymethyl]-2'-O,N-dibenzyloxycarbonyl-des-N-methyl-erythromycin A 9-oxime The product from Example 43(a) (130 mg) in methanol (5 ml) was treated with potassium carbonate (1.2 equiv.) and the mixture stirred at room temperature for ½ h. The methanol was evaporated and the residue taken up in ethyl acetate. Organic solution was washed with water and dried over anhydrous magnesium sulphate. Evaporation of the solvent and chromatography of the residue on silica-gel using ethyl acetate-hexane as eluent gave the title product as a colourless foam (90 mg); $\nu_{max}$. ($CHCl_3$) 1735 and 1690 cm$^{-1}$; $^{13}$C NMR δ (inter alia) 175.9 (C-1), 167.8 (C-9 oxime), 98.5 (OCH$_2$O), 69.33 and 67.07 (—OCH$_2$CH$_2$O—).

(c)
11-O-[2-Methanesulphonyloxyethoxymethyl]erythromycin A 9-oxime

The product from Example 43(b) (80 mg) was converted into the title compound by a procedure analogous to that described in Example 8(b). The title compound was obtained as a colourless foam (45 mg); $\nu_{max}$ ($CHCl_3$) 1720 cm$^{-1}$.

EXAMPLE 44

11-O-[2-Phthalimidoethoxymethyl]erythromycin A 9-oxime (a)
11-O-[2-Phthalimidoethoxymethyl]-2'-O,N-dibenzyloxycarbonyl-des-N-methyl erythromycin A-9-benzyloxycarbonyloxime The product from Preparation 2 (1 g) in dry dimethylformamide (5 ml) was treated with 2,6-lutidine (1.2 ml) and 2-phthalimidoethoxymethyl chloride (1.4 g) and the mixture stirred at room temperature for 4 h. The reaction mixture was poured into excess ethyl acetate and the organic solution washed successively with water, aqueous 20% citric acid solution, aqueous sodium bicarbonate solution, and finally brine. After drying over anhydrous magnesium sulphate the solvent was evaporated. Chromatography of the residue on silica-gel using ethyl acetate/hexane (1:1) as eluent gave the title product as a colourless foam (500 mg), $[\alpha]^{20}D$ −87.0° (c 1.0% in $CHCl_3$); $\nu_{max}$. ($CHCl_3$) 3450 and 1715 cm$^{-1}$; mass spectrum FAB-MS (3-nitrobenzyl alcohol matrix+sodium acetate) $MNa^+$ 1346 ($C_{71}H_{93}N_3O_{21}Na$).

(b) 11-O-[2-Phthalimidoethoxymethyl]erythromycin A 9-oxime

The product from Example 44(a) (240 mg) was converted into the title compound by a procedure analogous to that described in Example 8(b). The title compound was isolated as a colourless foam (115 mg), $[\alpha]^{20}D$ −59.9° (c 1.0% in $CHCl_3$); $\nu_{max}$ ($CHCl_3$) 3450 and 1710 cm$^{-1}$; mass spectrum FAB-MS (3-nitrobenzyl alcohol matrix+sodium acetate) $MNa^+$ 838 ($C_{48}H_{77}N_3O_{15}Na$).

EXAMPLE 45

11-O-[3-Benzoyloxypropyloxymethyl]-erythromycin A 9-oxime (a)
11-O-[3-Benzoyloxypropyloxymethyl]-2'-O,N-dibenzyloxycarbonyl-des-N-methylerythromycin A 9-benzyloxycarbonyloxime 2'-O,N-Dibenzyloxycarbonyl-des-N-methylerythromycin A-9-benzyloxycarbonyloxime (2.27 g) in dry DMF (12 ml) was treated with 2,6-lutidine (2.32 ml) and 3-benzoyloxypropyloxymethyl chloride (2.8 ml) and the mixture stirred at room temperature for 2 h. The solution was diluted with ethyl acetate (200 ml) and the organic solution washed successively with water, citric acid solution, aqueous sodium bicarbonate solution and finally brine. After drying over anhydrous magnesium sulphate the solvent was evaporated. Chromatography of the residue on silica-gel using ethyl acetate/hexane (1:1) as eluent gave the title product as a colouress foam (2 g), $[\alpha]^{20}D$ −68.7° (c 2.39% in $CHCl_3$); $\nu_{max}$. ($CHCl_3$) 1730 (br); mass spectrum FAB-MS (3-nitrobenzyl alcohol matrix+sodium acetate) $MNa^+$ 1351 ($C_{71}H_{96}N_2O_{22}Na$).

(b) 11-O-[3-Benzoyloxypropyloxymethyl]erythromycin A 9-oxime

The product from Example 45(a) (550 mg) in ethanol (30 ml) containing acetate buffer (3 ml; pH 4.8) was shaken with 10% Pd-C (250 mg) under 1 atmosphere of hydrogen hydrogenation continued for a further 1½ h. The catalyst was filtered off and the filter cake washed with ethanol. Evaporation gave an oil. The residue was taken up in water (20 ml) and the solution brought to pH 11 with potassium carbonate. The aqueous solution was extracted with ethyl acetate (2×100 ml) and the extracts washed with water. After drying over anhydrous magnesium sulphate, the solvent was evaporated to give a colourless foam. Chromatography on silica-gel using dichloromethane/methanol/ammonia (93:7:1) as eluent gave the title product as a colourless foam (350 mg); $\nu_{max}$ (CHCl$_3$) 1720 cm$^{-1}$; mass spectrum FAB-MS (3-nitrobenzyl alcohol matrix+sodium acetate) MNa$^+$ 963 (C$_{48}$H$_{80}$N$_2$O$_{16}$Na).

EXAMPLE 46

11-O-[2-Bromoethoxymethyl]erythromycin A 9-oxime (a) 11-O-[2-Bromoethoxymethyl]-2'-O,N-dibenzyloxycarbonyl-des-N-methylerythromycin A-9-benzyloxycarbonyloxime 2'-O,N-Dibenzyloxycarbonyl-des-N-methylerythromycin A 9-benzyloxycarbonyloxime (1.136 g) in dry dimethylformamide (6 ml) was treated with 2,6-lutidine (1.16 ml) and 2-bromoethoxymethyl chloride (1.04 g) and the mixture stirred at room temperature for 4 h. The solution was diluted with ethyl acetate (200 ml) and the organic solution washed successsively with water, aqueous citric acid solution, aqueous sodium bicarbonate solution and finally brine. After drying over anhydrous magnesium sulphate the solvent was evaporated. Chromatography of the residue on silica-gel using ethyl acetate/hexane (3:7) as eluent gave the title product as a colourless foam (0.6 g); $[\alpha]^{20}$D −85.0° (c, 3.0% wt/vol. in CHCl$_3$); $\nu_{max}$ (CHCl$_3$) 1730 and 1685 cm$^{-1}$; mass spectrum FAB-MS (3-nitrobenzyl alcohol matrix+sodium acetate) MNa$^+$ 1295 (C$_{63}$H$_{88}$N$_2$O$_{20}$BrNa).

(b) 11-O-[2-Bromoethoxymethyl]erythromycin A 9-oxime

The product from Example 46(a) was converted into the title compound using a procedure analogous to that desscribed in Example 8(b). Te title compound was thus obtained as a colourless foam; $[\alpha]^{20}$D −63.2° (c, 2.3% wt/vol. in CHCl$_3$); $\nu_{max}$ (CHCl$_3$) 1710, 1455 and 1160 cm$^{-1}$; mass spectrum FAB-MS (3-nitrobenzyl alcohol matrix+sodium acetate) MNa$^+$ 907 (C$_{40}$H$_{72}$N$_2$O$_{14}$BrNa).

EXAMPLE 47

11-O-[2-(Piperidin-1-yl)ethoxymethyl]erythromycin A 9-oxime (a) 11-O-[2-(Piperidin-1-yl)-ethoxymethyl]2'-O,N-dibenzyloxycarbonyl-des-N-methylerythromycin A 9-benzyloxycarbonyloxime The product from example 46(a) (0.6 g) in dry dimethyl formamide (10 ml) was treated with piperidine (9 equiv.) and the mixture heated in a sealed tube at 70° for 16 h. The mixture was poured into water (pH adjusted to 11 using potassium carbonate) and extracted with ethyl acetate. After drying over anhydrous magnesium sulphate the solvent was evaporated. Chromatography on silica-gel using chloroform:methanol:NH$_3$ (92:8:1) as eluent gave the title compound as a colourless foam (0.232 g) $[\alpha]^{20}$D −86.2° (c, 0.98% in CHCl$_3$); $\nu_{max}$ (CHCl$_3$) 1720 cm$^{-1}$; mass spectrum FAB-MS (3-nitro-benzyl alcohol matrix+sodium acetate) MNa$^+$ 1166 (C$_{60}$H$_{93}$N$_3$O$_{18}$Na).

(b) 11-O-[2-(Piperidin-1-yl)ethoxymethyl]erythromycin A-9-oxime

The product from Example (47(a) (0.232 g) was converted into the title compound by a procedure analogous to that described in Example 8(b). The title compound was isolated as a colourless foam (95 mg) $[\alpha]^{20}$D −66.9° (c, 1.0% in CHCl$_3$); $\nu_{max}$ (CHCl$_3$) 1720 cm$^{-1}$; mass spectrum FAB-MS (3-nitrobenzyl alcohol matrix+sodium aetate) MNa$^+$ 912 (C$_{45}$H$_{83}$N$_3$O$_{14}$Na).

EXAMPLE 48

11-O-[(2-N-Methyl-2-N-ethylamino)ethoxymethyl]erythromycin A 9-oxime (a) 11-O-[2-N-ethylamino)ethoxymethyl-2'-O,N-dibenzyloxycarbonyl-des-N-methyl-erythromycin A 9-benzyloxycarbonyloxime The product from Example 46(a) (0.5 g) in neat ethylamine (4 ml) was heated in a sealed tube at 70° for 4 h. The reaction mixture was poured into water and extracted with ethyl acetate at pH 11. After drying over anhydrous magnesium sulphate the solvent was evaporated and the residue chromatographed on silica-gel using chloroform:methanol:ammonia (90:10:1) as eluent to give the title compound as a colourless foam (208 mg), $[\alpha]^{20}$D −79.11° (c, 2.0% in CHCl$_3$); mass spectrum FAB-MS (3-nitrobenzyl alcohol matrix+sodium acetate) MNa$^+$ 1126 (C$_{57}$H$_{89}$N$_3$O$_{18}$Na).

(b) 11-O-[2-N-Methyl-2-ethylamino)ethoxymethyl]erythromycin A 9-oxime

The product from Example 48(a) (0.2 g) was converted into the title compound by a procedure analogous to that described in Example 8(b). The title compound was isolated as a colourless foam (155 mg), $[\alpha]^{20}$D −65.7° (c, 1.67% in CHCl$_3$); $\nu_{max}$ (CHCl$_3$) 1715 cm$^{-1}$; mass spectrum FAB-MS (3-nitrobenzyl alcohol matrix+sodium acetate) MNa$^+$ 886 (C$_{43}$H$_{81}$N$_3$O$_{14}$Na).

EXAMPLE 49

11-O-(N-Methyl-N-phenylsulphonamidomethyl)erythromycin A (a) 11-O-(N-Methyl-N-phenylsulphonamidomethyl)-2'-O,N-dibenzyloxycarbonyl-des-N-methyl erythromycin A 2'-O,N-Dibenzyloxycarbonyl-des-N-methyl erythromycin A (475 mg) was dissolved in dimethylformamide (5 ml) and 2,6-lutidine (295 μl) added followed by N-chloromethyl-N-phenylsulphonamide (330 mg) and the mixture stirred at room temperature for 3 h. The mixture was poured into excess ethyl acetate (60 ml) and the organic solution washed successively with water, 20% citric acid solution, aqueous sodium bicarbonate solution and finally dried over anhydrous magnesium sulphate. The solvent was evaporated and the residue chromatographed on silica-gel using 5% methanol in dichloromethane as eluent to give the title compound as a colourless foam (190 mg); $\nu_{max.}$ (CHCl$_3$) 3550, 1730, 1690 and 690 cm$^{-1}$; $^{13}$C NMR (CDCl$_3$) δ (inter alia) 218.1 (C-9 ketone), 178.8, 176.3 and 175.7 (C-1), 110.1 and 108.8 (C-9 of hemi-ketals), 85.8 and 85.3 (C-6 of hemi-ketals), 82.8 and 80.9 (O—$\underline{CH_2}$—N), 76.0 (C-6 of 9-keto compound); mass spectrum FAB-MS (3-nitrobenzyl alcohol matrix+sodium acetate) MNa$^+$ 1193 (C$_{60}$H$_{86}$N$_2$O$_{19}$SNa). The title product exists in deuteriochloroform solution as a mixture of 9-keto and two 6,9-hemiketal tautomers.

(b) 11-O-(N-Methyl-N-phenylsulphonamidomethyl) erythromycin A

The product from Example 49(a) (190 mg) was converted into the title compound by a procedure analogous to that described in Example 8(b). The title compound was obtained as a colourless foam (96 mg); $\nu_{max.}$ (CHCl$_3$) 3700, 3300 and 1710 cm$^{-1}$; $^{13}$C NMR (CDCl$_3$) δ (inter alia) 218.2 (C-9 ketone), 179.0, 176.6 and 175.9 (C-1), 110.3 and 108.4 (C-9 of hemi-ketals), 104.7 and 102.9 (C-1'), 97.1 and 96.2 C-1''), 85.5 and 85.2 (C-6 of hemi-ketals), 80.9, 80.3 and 79.8 (O—$\underline{CH_2}$—N), 76.1 (C-6 of 9-keto compound); mass spectrum FAB-MS (3-nitro- benzyl alcohol matrix+sodium acetate) MNa$^+$ 939; MH$^+$ 917; EI 899 (M$^+$—H$_2$O); (M$^+$—H$_2$O) 898.4835, C$_{45}$H$_{74}$N$_2$O$_{14}$S requires M 898.4865. The title compound exists in deuterochloroform solution as a mixture of 9-keto and two 6,9-hemiketal tautomers.

EXAMPLE 50

11-O-[2-Methoxyethoxymethyl]erythromycin A-6,9-hemi-ketal (a)
11-O-[2-Methoxyethoxymethyl]-2'-O,N-dibenzyloxycarbonyl-des-N-methylerythromycinyn A-6,9 hemi-ketal 2'-O,N-Dibenzyloxycarbonyl-des-N-methylerythromycin A (830 mg) in dry DMF (5 ml) was treated with 2,6-lutidine (0.6 ml) and 2-methoxyethoxymethyl chloride (0.36 g) and the mixture stirred at room temperature for 1 h. The solution was diluted with ethyl acetate (150 ml) and the organic solution washed successively with water, citric acid solution, aqueous sodium bicarbonate and finally brine. After drying over anhydrous magnesium sulphate the solvent was evaporated. Chromatography of the residue on silicagel using ethyl acetate/hexane (2:1) as eluent gave the title compound (mixture of hemi-ketal tautomers) as a colourless foam (500 mg), $\nu_{max.}$ (CHCl$_3$) 1730 and 1690 cm$^{-1}$; mass spectrum FAB-MS (3-nitrobenzyl alcohol matrix+sodium acetate) MNa$^+$ 1098 (C$_{56}$H$_{85}$NO$_{19}$Na).

(b) 11-O-[2-Methoxyethoxymethyl]erythromycin A-6,9-hemi-ketal

The product from Example 50(a) (300 mg) was converted into the title compound by a procedure analogous to that described in Example 8(b). The title compound was (CHCl$_3$) 1720 cm$^{-1}$; mass spectrum FAB-MS (3-nitrobenzyl alcohol matrix+sodium acetate) MNa$^+$ 844 (C$_{41}$H$_{75}$NO$_{15}$Na).

EXAMPLE 51

11-O-[2-Bromoethoxymethyl]erythromycin A-6,9-hemi-ketal (a)
11-O-[2-Bromoethoxymethyl]-2'-O,N-dibenzyloxycarbonyl-des-N-methylerythromycin A-6,9-hemi-ketal 2'-O,N-Dibenzyloxycarbonyl-des-N-methylerythromycin A (1 g) in dry dimethylformamide (6 ml) was treated with 2,6-lutidine (1.2 ml) and 2-bromoethoxymethyl chloride (0.84 g) and the mixture stirred at room temperature for 4 h. Excess ethyl acetate was added and the organic solution washed successively with water, aqueous citric acid solution, aqueous sodium bicarbonate solution and finally brine. After drying over anhydrous magnesium sulphate the solvent was evaporated to give a colourless foam. Chromatography of the residue on silica-gel using ethyl acetate/hexane (2:1) as eluent gave the product as a colourless foam (500 mg), $\nu_{max.}$ (CHCl$_3$) 1720 and 1690 cm$^{-1}$; mass 2 spectrum FAB-MS (3-nitrobenzyl alcohol matrix+sodium acetate) MNa$^+$ 1146 (C$_{55}$H$_{82}$NO$_{18}$Br).

(b) 11-O-[2-Bromoethoxymethyl]erythromycin A-6,9-hemi-ketal

The product from Example 51(a) (300 mg) was converted into the title compound by a procedure analogous to that described in Example 8(b). The title compound was isolated as a colourless foam (200 mg), $\nu_{max.}$ (CHCl$_3$) 3450 and 1720 cm$^{-1}$; mass spectrum (3-nitrobenzyl alcohol matrix+sodium acetate) MNa$^+$ 892 (C$_{40}$H$_{72}$NO$_{14}$Br).

EXAMPLE 52

11-O-[2-N,N-Dimethylaminoethoxymethyl]erythromycin A-6,9- hemi-ketal (a)
11-O-[2-N,N-Dimethylaminoethoxymethyl]-2'-O,N-dibenzyl-oxycarbonyl-des-N-methylerythromycin A 6,9-hemi-ketal The product from Example 51(a) was dissolved in dry dimethylformamide (2 ml) and the mixture cooled to 0°-5°. Dry dimethylamine gas was bubbled into the solution for a few minutes (uptake was ca. 300 mg) and the mixture heated in a sealed tube at 80° for 3 h. Nitrogen was blown through the solution to remove excess dimethylamine and the solution poured into excess water. The solution was adjusted to pH 11 with potassium carbonate solution and extracted with ethyl acetate (2×50 ml). After drying over anhydrous magnesium sulphate the solvent was evaporated to give a colourless foam. Chromatography of the residue on silica-gel using CHCl$_3$: MeOH:NH$_3$ (90:10:1) as eluent gave the title compound as a mixture of hemi-ketal tautomers (160 mg), $\nu_{max.}$ (CHCl$_3$) 1730, 1690 and 1675 cm$^{-1}$; mass spectrum FAB-MS (3-nitrobenzyl alcohol matrix+sodium acetate) MNa$^+$ 1111 (C$_{57}$H$_{88}$N$_2$O$_{18}$Na).

(b)
11-O-[2-N,N-Dimethylaminoethoxymethyl]erythromycin A-6,9-hemi-ketal

The product from Example 52(b) (150 mg) was converted into the title compound by a procedure analogous to that described in Example 8(b). The title compound was isolated as a colourless foam (100 mg), $\nu_{max.}$ (CHCl$_3$) 1720 cm$^{-1}$; mass spectrum FAB-MS (3-nitrobenzyl alcohol matrix+sodium acetate) MNa+ 857 ($C_{42}H_{78}N_2O_{14}Na$).

EXAMPLE 53

11-O-[2-Benzoyloxyethoxymethyl]erythromcin A 9-imine

11-O-[2-Benzoyloxyethoxymethyl]erythromycin A-9-oxime (500 mg) in methanol (5 ml) was treated with ammonium acetate (1 g) and the solution stirred under nitrogen. An aqueous solution of ca. 15% titanium trichloride (ca. 1.3 ml) was added until the colour persisted and the mixture stirred for a further 25 min. The mixture was partitioned between water (pH adjusted to 10) and diethyl ether. The organic layer was dried over anhydrous magnesium sulphate and the ether evaporated to give the title compound as a colourless foam (330 mg); $v_{max}$ (CHCl$_3$) 3450 and 1720 cm$^{-1}$; $^{13}$C NMR (CDCl$_3$) δ (inter alia) 177.1 (C-1), 166.4 (PhCO.O) 96.5 (O—CH$_2$—O), 95.6 (C-9), 82.4 (C-6), 66.7 and 63.9 (O$\underline{CH_2}$CH$_{O2}$CPh and OCH$_2$$\underline{CH_2}$O$_2$CPh); mass spectrum FAB-MS (3-nitrobenzyl alcohol matrix+sodium acetate) MNa+ 933 ($C_{47}H_{78}N_2O_{15}Na$) MH+ 911 ($C_{47}H_{79}N_2O_5$). These data show that the title compound exists in deuterochloroform as the 6,9-carbinolamine tautomer.

EXAMPLE 54

11-O-[2-Benzoyloxyethoxymethyl]-erythromycylamine A

11-O-[2-Benzoyloxyethoxymethyl]erythromycin A-9-imine (200 mg) in methanol (4 ml) was treated with sodium borohydride (20 mg) and the mixture stirred at room temperature for 1 h. The pH was adjusted to 2.5 using 20% aqueous citric acid solution and the mixture stirred for a further 5 min. Water was now added and the aqueous solution extracted with dichloromethane at pH 6, pH 7, pH 8 and pH 9. The amine containing extracts (pH 7) were combined, washed with water and dried over anhydrous magnesium sulphate. Evaporation of the solvent gave a colourless foam. Chromatography of the residue on silica-gel using dichloromethane:methanol:ammonia (93:7:1) as eluent gave the title product as a colourless foam (140 mg), $[α]^{20}D$ −45.6 (c, 1.0% in CHCl$_3$); $v_{max}$ (CHCl$_3$) 1720 cm$^{-1}$; $^{13}$C NMR (CDCl$_3$) δ (inter alia) 176.0 (C-1), 166.4 (PhCOO), 98.9 (O—CH$_2$—O), 76.6 (C-6), 67.1 and 64.01 (O$\underline{CH_2}$CH$_2$O$_2$CPh and OCH$_2$$\underline{CH_2}$O$_2$CPh), 62.1 (C-9); mass spectrum FAB-MS (3-nitrobenzyl alochol matrix) MH+ 913 ($C_{47}H_{81}N_2O_{15}$).

EXAMPLE 55

11-O-(2-Methoxyethoxymethyl]erythromycin A 9-imine

11-O-[2-Methoxyethoxymethyl]erythromycin A 9-oxime (600 mg) in methanol (10 ml) was treated with ammonium acetate (1.2 g) and the mixture stirred under nitrogen. An aqueous solution ca. 15% titanium trichloride was added until the colour persisted and the mixture stirred for a further 35 min. The mixture was partitioned between water (pH adjusted to 10) and diethyl ether. The organic layer was dried over anhydrous magnesium sulphate and the ether evaporated to give the title compound as a colourless foam (485 mg), $v_{max}$ (CHCl$_3$) 3450 and 1720 cm$^{-1}$; $^{13}$C NMR (CDCl$_3$) δ (inter alia) 177.1 (C-1), 96.5 (O—CH$_2$—O), 95.6 (C-9), 82.44 (C-6) 71.8 and 67.35 (O$\underline{CH_2}$$\underline{CH_2}$OMe), 59.1 (MeO); mass spectrum FAB-MS (3-nitrobenzyl alcohol matrix) MH+ 821 ($C_{41}H_{77}N_2O_{14}$).

EXAMPLE 56

11-O-[2-Methoxyethoxymethyl]erythromycylamine A

11-O-[2-Methoxyethoxymethyl]erythromycin A-9-imine (175 mg) in methanol (4 ml) was treated with sodium borohydride (20 mg) and the mixture stirred at room temperature for 1 h. The pH was adjusted to 2.5 using 20% aqueous citric acid solution and the mixture stirred for a further 5 min. Water was added and the aqueous solution extracted with dichloromethane at pH 6, 7, 8, 9 and 10. The amine containing extracts were dried over anhydrous magnesium sulphate and the solvent evaporated. Chromatography of the residue on silica-gel using dichloromethane:methanol:ammonia (93:7:1) as eluent gave the title compound as a colourless foam (100 mg), $[α]^{20}D$ −37.2° (c, 1.0% in CHCl$_3$); $v_{max}$ (CHCl$_3$) 1720 cm$^{-1}$; $^{13}$C NMR (CDCl$_3$) δ (inter alia) 176.2 (C-1), 98.7 (O—CH$_2$—O), 76.24 (C-6), 71.65 and 68.39 (O$\underline{CH_2}$$\underline{CH_2}$OMe), 62.31 (C-9), 58.8 (MeO); mass spectrum FAB-MS (3-nitrobenzyl alcohol matrix) MH+ 823 ($C_{41}H_{79}N_2O_{14}$).

EXAMPLE 57

11-O-[Ethoxymethyl]-erythromycin A 9-imine

11-O-[Ethoxymethyl]-erythromycin A 9-oxime (800 mg) in methanol (8 ml) was treated with ammonium acetate (1.6 g) and the solution stirred under nitrogen. An aqueous solution of ca. 15% titanium trichloride was added until the colour persisted and the mixture stirred for a further 30 min. The mixture was partitioned between water (pH adjusted to 10) and diethyl ether. The organic layer was dried over anhydrous magnesium sulphate and the ether evaporated to give the title compound as a colourless foam (400 mg), $v_{max}$ (CHCl$_3$) 3450 and 1720 cm$^{-1}$. $^{13}$C NMR (CDCl$_3$) δ (inter alia) 177.2 (C-1), 95.9 (O—CH$_2$O), 95.42 (C-9, H$_2$N—C—O), 82.32 (C-6), 64.12 (C$\underline{H_3}$$\underline{CH_2}$O). These data show that the title compound exists in deuterochloroform as the 6,9-carbinolamine-tautomer.

EXAMPLE 58

11-O-[Ethoxymethyl]erythromycylamine A

11-O-[Ethoxymethyl]erythromycin A-9-imine (350 mg) in methanol (7 ml) was treated with sodium borohydride (35 mg) and the mixture stirred at room temperature for 1 h. The same work-up and isolation procedures described in Example 56 gave the title compound as a colourless foam (250 mg); $[α]^{20}D$ −35.8° (c, 1.0% in CHCl$_3$); $v_{max}$ (CHCl$_3$) 1720 cm$^{-1}$; $^{13}$C NMR (CDCl$_3$) δ (inter alia) 176.0 (C-1), 98.42 (O—CH$_2$—O), 76.48 (C-6), 64.28 (CH$_3$$\underline{CH_2}$O—), 62.25 (C-9); mass spectrum FAB-MS (3-nitrobenzyl alcohol matrix+sodium acetate) MNa+ 815 ($C_{40}H_{76}N_2O_{13}Na$).

EXAMPLE 59

11-O-[2-Hydroxyethoxymethyl]erythromycin A-9-imine

11-O-[2-Hydroxyethoxymethyl]erythromycin A-9-oxime (780 mg) in methanol (10 ml) was treated with ammonium acetate (2 g) and the mixture stirred under nitrogen. An aqeuous solution of ca. 15% titanium trichloride was added until the colour persisted and the mixture stirred for a further 30 min. The same work-up and isolation procedures described in Example 55 gave the title compound as a colourless foam (688 mg), $\nu_{max.}$ (CHCl$_3$) 1720 cm$^{-1}$; $^{13}$C NMR (CDCl$_3$) δ (inter alia) 178.2 (C-1), 98.47 (—OCH$_2$O—), 94.9 (C-9), 82.6 (C-6), 72.78 and 62.26 (—OCH$_2$CH$_2$OH and —OCH$_2$CH$_2$OH). Mass spectrum FAB-MS (3-nitrobenzyl alcohol matrix+sodium acetate) MNa$^+$ 829 (C$_{40}$H$_{74}$N$_2$O$_{14}$), MH$^+$ 807 (C$_{40}$H$_{73}$N$_2$O$_{14}$). These data show that the title imine exists in deuterochloroform solution as the 6,9-carbinolamine ether tautomer.

EXAMPLE 60

11-O-[2-Hydroxyethoxymethyl]erythromycylamine A

11-O-[2-Hydroxyethoxymethyl]erythromycin A 9-imine (680 mg) in methanol (14 ml) was treated with sodium borohydride (70 mg) and the mixture stirred at room temperature for 1 h. The same work-up and isolation procedures as described in Example 56 gave the title compound as a colourless foam (200 mg) $[\alpha]^{20}$D −53.2° (c, 1.0% in CHCl$_3$); $\nu_{max.}$ (CHCl$_3$) 1720 cm$^{-1}$; $^{13}$C NMR (CDCl$_3$) δ (inter alia) 176.34 (C-1), 99.29 (O—CH$_2$—O), 71.27 and 61.61 (—OCH$_2$CH$_2$OH and OCH$_2$CH$_2$OH), 62.67 (C-9); mass spectrum FAB-MS (3-nitrobenzyl alcohol matrix+sodium acetate) MNa$^+$ 831 (C$_{40}$H$_{76}$N$_2$O$_{14}$Na).

EXAMPLE 61

11-O-[2-N,N-Dimethylaminoethoxymethyl]erythromycin A 9-imine

11-O-[2-N,N-Dimethylethoxymethyl]erythromycin A 9-oxime (450 mg) in methanol (8 ml) was treated ammonium acetate (1 g) and the mixture stirred under nitrogen. An aqueous ca. 15% solution of titanium trichloride was added until the colour persisted and the mixture stirred at room temperature for 50 min. The same work-up and isolation procedures described in Example 55 gave the title compound as a colourless foam (380 mg). $\nu_{max.}$ (CHCl$_3$) 1720 cm$^{-1}$. The $^{13}$C NMR showed that the title imine existed in deuterochloroform as the 6,9-carbinolamine tautomer.

EXAMPLE 62

11-O-[2,N,N-Dimethylamimoethoxymethyl]erythromycyl amine A

11-O-[2-N,N-Dimethylethoxymethyl]erythromycin A 9-imine (380 mg) in methanol (8 ml) was treated with sodium borohydride (40 mg) and the mixture stirred at room temperature for 1 h. The same work-up and isolation procedures described in Example 56 gave the title compound as a colourless foam (270 mg); $[\alpha]^{20}$D −28.8° (c, 1.0% in CHCl$_3$); $\nu_{max.}$ (CHCl$_3$) 3450 and 1720 cm$^{-1}$; $^{13}$C NMR (CDCl$_3$) δ (inter alia) 176.2 (C-1), 99.2 (—OCH$_2$O—), 75.63 (C-6), 67.8 and 59.4 (OCH$_2$CH$_2$OH and OCH2CH$_2$OH), 62.5 (C-9).

EXAMPLE 63

11-O-[3-Propyloxymethyl]erythromycin A 9-imine

11-O-[3-Propyloxymethyl]erythromycin A 9-oxime (290 mg) in methanol (5 ml) containing ammonium acetate (1 g) was stirred at room temperature under nitrogen. An aqueous solution of ca. 15% titanium trichloride was added until the colour persisted and the solution stirred for a further 40 mins. The same work-up and isolation procedures described in Example 55 gave the title compound as a colourless foam (175 mg). $\nu_{max.}$ (CHCl$_3$) 1720 cm$^{-1}$ The 13C NMR showed that the title compond existed as the 6-9-carbinolamine tautomer in deuterochloroform solution.

EXAMPLE 64

11-O-[3-Propyloxymethyl]erythromycylamine A

11-O-[3-Propyloxymethyl]erythromycin A-9-imine (170 mg) in methanol (5 ml) was treated with sodium borohydride (30mg) and the mixture stirred at room temperature for 1 h. The same work-up and isolation procedures described in Example 56 gave the title compound as a colourless foam (160 mg), $[\alpha]^{20}$D −33.5° (c, 1.0 in CHCl$_3$); $\nu_{max.}$ (CHCl$_3$) 1720 cm$^{-1}$; mass spectrum FAB-MS (3-nitrobenzyl alcohol matrix+sodium acetate) MNa$^+$949 (C$_{48}$H$_{82}$N$_2$O$_{15}$Na).

I claim:

1. A compound of the formula I:

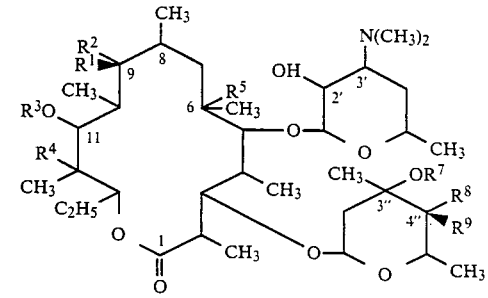

a pharmaceutically acceptable acid addition salt thereof or a pharmaceutically acceptable ester thereof wherein one of R$^1$ and R$^2$ is hydrogen and the other of R$^1$ and R$^2$ is an amino group of the formula V

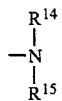

wherein R$^{14}$ and R$^{15}$ are the same or different and each is hydrogen, a hydrocarbon of up to 18 carbon atoms, unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclylthio, arylthio, sulphamoyl, carbamoyl, amidino, guanidino, nitro, halo, carboxyl or a salt or ester thereof, acyl or acyloxy; or R$^1$ and R$^2$ together form an oxo group, an oxime group of the formula IV,

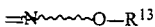 IV or an imino group, wherein R$^{13}$ is hydrogen, a hydrocarbon of up to 18 carbon atoms unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclythio, arylthio, sulphamoyl, carbamoyl, amidino, guanidino, nitro, halo, carboxyl or a salt or ester thereof, acyl or acyloxyl; and wherein the wavy line in formula IV means the compounds can exist in the E- and Z-geometric isomeric forms about the C═N double bond at the 9-position; $R^5$ is hydroxy or alkoxy of up to 12 carbon atoms; or one of $R^1$ and $R^2$ is hydroxy, or amino, and the other of $R^1$ and $R^2$ together with $R^5$ forms an ether oxygen atom, —O—, $R^3$ is a group of the formula II:

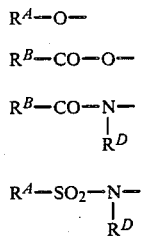

in which Q is:

$R^A$—O—    IIIA $R^B$—CO—O—    IIIB $$R^B-CO-N-\atop{\phantom{xx}|\atop R^D}$$    IIIC $$R^A-SO_2-N-\atop{\phantom{xx}|\atop R^D}$$    IIID wherein $R^A$ is a hydrocarbon of up to 18 carbon atoms unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclythio, arylthiuo, sulpyhamoyl, carbamoyl, amidino, guanidino, nitro, halo, carboxyl or a salt or ester thereof, acyl or acyloxyl, $R^B$ is hydrogen, a hydrocarbon of up to 18 carbon atoms unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclylthio, arylthio, sulphamoyl, carbamoyl, amidino, guanidino, nitro, halo, carboxyl or a salt or ester thereof, acyl or acyloxy or a hydrocarbon-oxy of up to 18 carbon atoms unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbonm atoms in the alkyl moiety, heterocyclylthio, arylthio, sulphamoyl, carbamoyl, amidino, guanidino, nitro, halo, carboxyl or a salt or ester thereof, acyl or acyloxyl; each of $R^C$ and $R^D$, are the same or different, and each is hydrogen, a hydrocarbon of up to 18 carbon atoms unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclythio, arylthio, sulphamoyl, carbamoyl, amidino, guanidino, nitro, halo, carboxyl or a salt or ester thereof, acyl or acyloxyl, or any two of $R^A$, $R^B$, $R^C$ and $R^D$ are a divalent, organic group forming together with the intervening atoms of the molecule a 4- to 7-membered heterocylic ring having up to 4 heteroatoms selected from the group consisting of oxygen, nitrogen and sulphur unsubstituted or substituted by up to 3 substituents selected from the group consisting of halo, alkyl of 1 to 6 carbon atoms, alkoxy of 1 to 6 carbon atoms, haloalkyl of 1 to 6 carbon atoms, hydroxy, amino, carboxyl or a salt or ester thereof, alkoxycarobnyl of 1 to 6 carbon atoms in the alkoxy moiety, alkoxycarbonylalkyl of 1 to 6 carbon atoms in each of the alkoxy and alkyl moieties, aryl and oxo;

$R^4$ is hydrogen or hydroxy;
$R^7$ is hydrogen or methyl;
one of $R^8$ and $R^9$ is hydrogen, hydroxy, alkoxy of 1 to 12 carbon atoms, alkanoyloxy of 1 to 12 carbon atoms, an amino group of the formula V $$-N{R^{14}\atop|\atop R^{15}}$$    V wherein $R^{14}$ and $R^{15}$ are as above defined, or a group of the formula $R^{12}$—SO$_2$—O—, and the other of $R^8$ and $R^9$ is hydrogen, or $R^8$ and $R^9$ together form an oxo group or an oxime group of the formual IV

=N~~~O—$R^{13}$    IV wherein $R^{13}$ is as above defined; the wavy line in formula IV has the meaning set forth above; and $R^{12}$ is a hydrocarbon of up to 18 carbon atoms, oxahydrocarbon of up to 18 carbon atms, thiahydrocarbon of up to 18 carbon atoms or azahydrocarbon of up to 18 carbon atoms, each of which is either unsubstituted or substituted by heterocyclyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclythio, arylthio, sulphamoyl, carbamoyl, amidino, guanidino, nitro, halo, carboxyl or a salt or ester thereof, acyl or acyloxy.

2. A compound according to claim 1, wherein $R^3$ is of the formula $R^A$—O—CH$_2$—

$R^B$—CO—NH—CH$_2$—

$$R^B-CO-N-CH_2-\atop{\phantom{xxxxx}|\atop R^E}$$

or

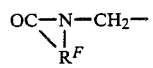

in which
$R^A$ is a hydrocarbon of up to 18 carbon atoms, unsubstituted or substituted by heterocyyl, amino, alkanoylamino of 1–6 carbon atoms in the alkyl moiety, mono-, di-, or tri-alkylamino of 1–6 carbon atoms in each alkyl moiety, hydroxy, alkoxy of 1–6 carbon atoms, mercapto, alkylthio of 1–6 carbon atoms in the alkyl moiety, heterocyclthio, arylthio, sulphamoyl, carbamoyl, amidino, guanidino, nitro, halo, carboxyl or a salt or ester thereof, acyl or acyloxyl and $R^B$ is hydrogen, a hydrocarbon of up to 18 carbon atoms or a hydrocarbon-oxy of up to 18 carbon atoms, said hydrocarbon and said hydrocarbon-oxy being unsubstituted or substituted by heterocyyl, amino, alkanoylamino of 1–6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclthio, arylthio, sulphamoyl, carbamoyl, amidino, guanidinom, nitro, halo, carboxyl or a salt or ester thereof, acyl or acyloxyl, $R^E$ is a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclthio, arylthio, sulphamoyl, carbamoyl, amidino, guanidino, nitro, halo, carboxyl or a salt or ester thereof, acyl or acyloxyl, and $R^F$ is a divalent hydrocarbon completing a 4- to 7-membered ring unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclthio, arylthio, sulphamoyl, carbamoyl, amidino, guanidino, nitro, halo, carboxyl or a salt or ester thereof, acyl or acyloxyl.

3. A compound according to claim 1, wherein $R^4$ is 2-substituted-ethyl or 3-substituted-propyl, in which the substituent is amino, N-alkylamino, N,N-dialkylamino, halogen, hydroxy, alkoxy, benzoyloxy, alkanesulphonyloxy, trisilyloxy, alkoxycarbonyl, alkanoyloxy, phenoxy, or heterocyclyl.

4. A compound according to claim 1, wherein $R^{13}$ is hydrogen or methyl.

5. A compound according to claim 1, wherein $R^4$ is hydroxy.

6. A compound according to claim 1, wherein $R^5$ is hydroxy.

7. A compound according to claim 1, wherein $R^7$ is methyl.

8. A compound according to claim 1, wherein $R^8$ is hydrogen and $R^9$ is hydroxy.

9. 11-O-[2-Dimethylaminoethoxymethyl]-erythromycin A 9-methoxime.

10. A compound of the formula IX

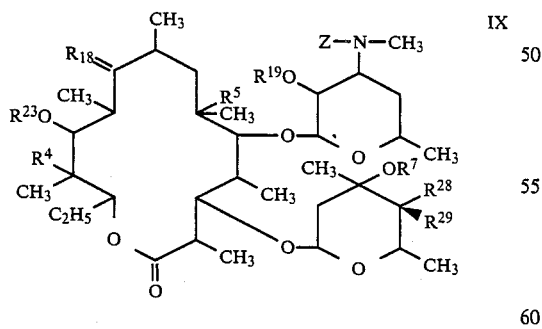

in which
$R^4$ is hydrogen or hydroxy, $R^5$ is hydroxy or alkoxy and $R^7$ is hydrogen or methyl;
$R^{18}$ is an oxo group, an oxime group of the formual IV

=N~~O—R¹³            IV wherein $R^{13}$ is hydrogen, a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclthio, arylthio, sulphamoyl, carbamoyl, amidino, guanidino, nitro, halo, carboxyl or a salt or ester thereof, acyl or acyloxyl;

$R^{19}$ is H or Z;

$R^{23}$ is H or $R^3$ wherein $R^3$ is a group of the formula II:

$$Q-\underset{R^C}{CH}-  \qquad\qquad II$$

in which
Q is:

$$R^A-O- \qquad\qquad IIIA$$

$$R^B-CO-O- \qquad\qquad IIIB$$

$$R^B-\underset{R^D}{CO-N}- \qquad\qquad IIIC$$

$$R^A-\underset{R^D}{SO_2-N}- \qquad\qquad IIID$$

wherein $R^A$ is a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclthio, arylthio, sulpyamoyl, carbamoyl, amidino, guanidino, nitro, halo, carboxyl or a salt or ester thereof, acyl or acyloxyl, $R^B$ is hydrogen a hydrocarbon of up to 18 carbon atoms or a hydrocarbon-oxy of up to 18 carbon atoms, each of which may be unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms mercapto, alkylthio of 1-6 carbon atoms in the alkyl moiety, heterocyclthio, arylthio, sulphamoyl, carbamoyl, amidino, guanidino, nitro, halo, carboxyl or a salt or ester thereof, acyl or acyloxyl, each of $R^C$ and $R^D$, are the same or different, and each is hydrogen or a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxyl, alkoxy of 1-6 carbon atoms, mercapto, alkylthio of 1-6 carbon atoms in the alkyl moiety, heterocyclthio, arylthio, sulphamoyl, carbamoyl, amidino, guanidino, nitro, halo, carboxyl or a salt or ester thereof, acyl or acyloxyl, or any two of $R^A$, $R^B$, $R^C$ and $R^D$ are a divalent organic group forming together with the intervening atoms of the molecule a 4- to 7-membered heterocyclic ring having up to 4 heteroatoms selected from the group consisting of oxygen, nitrogen and sulphur unsubstituted or substituted by up to 3 substituents selected from the group consisting of halo, alkyl of 1 to 6 carbon atoms, alkoxy of 1 to 6 carbon atoms, haloalkyl of 1 to 6 carbon atoms, hydroxy amino, carboxyl or a salt or ester thereof, alkoxycarbonyl of 1 to 6 carbon atoms in the alkoxy moiety, alkoxycarbonylalkyl of 1 to 6 carbon atoms in each of the alkoxy and alkyl moieties, aryl and oxo, with the proviso that, if $R^{18}$ is oxo or $R^5$ is methoxy, then $R^{23}$ is $R^3$; one of $R^{28}$ and $R^{29}$ is H, OH, OZ, $NZ_2$, amino of the formula V

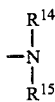

wherein $R^{14}$ and $R^{15}$ are the same or different and each is hydrogen, a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocylthio, arylthio, sulphamoyl, carbamoyl, amidino, guanidino, nitro, halo, carboxyl or a salt or ester thereof, acyl or acyloxyl, NHZ unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms mercapto, alkylthio of 1-6 carbon atoms in the alkyl moiety, heterocycylthio, arylthio, sulphamoyl, carbamoyl, amidino, guanidino, nitro, halo, carboxyl or a salt or ester theroef, acyl or acyloxyl, alkoxy of 1 to 12 carbon atoms, alkanoyloxy of 1 to 12 carbon atoms in the alkyl moiety, or $R^{12}$—$SO_2$—$O$— in which $R^{12}$ is a hydrocarbon of up to 18 carbon atoms, oxahydrocarbon of up to 18 carbon atoms, thiahydrocarbon of up to 18 carbon atoms or azahydrocarbon of up to 18 carbon atoms, each of which is either unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxyl, and the other of $R^{28}$ and $R^{29}$ is H, or $R^{28}$ and $R^{29}$ together are oxo; and Z is benzyloxy-carbonyl unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arlthio, sulphamoyl, carbamoyl, amidino, guanidino, nitro, halo, carboxyl or a salt or ester thereof, acyl or acyloxyl.

11. A compound according to claim 3 wherein $R^4$ is 2-substituted-ethyl or 3-substituted-propyl in which the substituent is a nitrogen-containing heterocylcyl having from 4-7 ring atoms which is bonded through a ring nitrogen atom.

12. A compound according to claim 3 wherein $R^4$ is 2-substituted-ethyl or 3-substituted-propyl in which the substituent is triazolyl, piperidinyl or phthalimido bonded through a ring nitrogen atom.

13. 11-O-(2-piperidin-1-yl)-ethyloxymethyl)-erythromycin A 9-O-methoxime.

14. A pharmaceutical composition useful for treating bacterial infections in humans and animals which comprises an antibacterially effective amount of a compound of the formula I

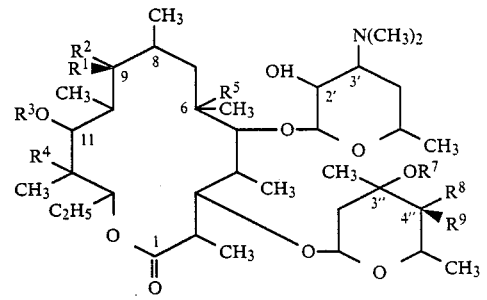

a pharmaceutically acceptable acid addition salt thereof or a pharmaceutically acceptable ester thereof wherein one of $R^1$ and $R^2$ is hydrogen and the other of $R^1$ and $R^2$ is an amino group of the formula V

wherein $R^{14}$ and $R^{15}$ are the same or different and each is hydrogen, a hydrocarbon of up to 18 carbon atoms, unsubstituted of substituted by hetercyclyl, amino, alikanoylamino of 1-6 atoms in the alkyl moiety, mono-, di-, or tri-alkylamino of 1-6 carbon atoms in each alkyl moiety, hydroxyl, alkoxy of 1-6 carbon atoms, mercapto, alkylthio of 1-6 carbon atoms in the akyl moiety, heterocyclythio, arylthio, sulphamoyl, carbamoyl, amidino, guanidino, nitro, halo, carboxyl or a salt or ester thereof, acyl or acyloxyl; or $R^1$ and $R^2$ together form an oxo group, an oxime group of the formula IV,

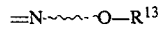
=N—∿∿—O—$R^{13}$    IV or an imino group, wherein $R^{13}$ is hydrogen, a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6ccarbon atoms in each alkyl moiety, hydroxy, alkoxy of 1-6 carbon atoms, mercapto, alkylthio of 1-6 carbon atoms in the alkyl moiety, heterocyclythio, arylthio, sulphamoyl, carbamoyl, amidino, guanidino, nitro, halo, carboxyl or a salt or ester thereof, acyl or acyloxy; and wherein the wavy line in formula IV means the compounds can exist in the E- and Z-geometric isomeric forms about the C=N double bond at the 9-position; $R^5$ is hydroxy or alkoxy of up to 12 carbon atoms; or one of $R^1$ and $R^2$ is hydroxy, or amino, and the other of $R^1$ and $R^2$ together with $R^5$ forms an ether oxygen atom, —O—, $R^3$ is a group of the formula II:

$$Q-\underset{R^C}{\overset{|}{CH}}-\quad\quad\text{II}$$

in which Q is:

$$R^A-O-\quad\quad\text{IIIA}$$

$$R^B-CO-O-\quad\quad\text{IIIB}$$

$$R^B-CO-\underset{R^D}{\overset{|}{N}}-\quad\quad\text{IIIC}$$

$$R^A-SO_2-\underset{R^D}{\overset{|}{N}}-\quad\quad\text{IIID}$$

wherein $R^A$ is a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclythio, arylthio, sulphamoyl, carbamoyl, amidino, guanidino, nitro, halo, carboxyl or a salt or ester thereof, acyl or acyloxy $R^B$ is hydrogen, a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxy or a hydrocarbon-oxy of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclthio, arylthio, sulphamoyl, carbamoyl, amidino, guanidino, nitro, halo, carboxyl, or a salt or ester thereof, acyl or acyloxyl; each of $R^C$ and $R^D$, are the same or different, and each is hydrogen, a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto alkylthio of 1-6 carbon atoms in the alkyl moiety, heterocyclythio, arylthio, sulphamoyl, carbamoyl, amidino, guanidino, nitro, halo, carboxyl or a salt or ester thereof, acyl or acyloxyl, or any two of $R^A$, $R^B$, $R^C$ and $R^D$ are a divalent, organic group forming together with the intervening atoms of the molecule a 4- to 7-membered heterocyclic ring having up to 4 heteroatoms selected from the group consisting of oxygen, nitrogen and sulphur unsubstituted or substituted by up to 3 substituents selected form the group consisting of halo, alkyl of 1 to 6 carbon atoms, hydroxy, amino carboxyl or a salt or ester thereof, alkoxycarbonyl of 1 to 6 carbon atoms in the alkoxy moiety, alkoxycarbonylalkyl of 1 to 6 carbon atoms in each of the alkoxy and alkyl moieties, aryl and oxo;

$R^4$ is hydrogen or hydroxy;
$R^7$ is hydrogen or methyl;

one of $R^8$ and $R^9$ is hydrogen, hydroxy, alkoxy of 1 to 12 carbon atoms, alkanoyloxy of 1 to 12 carbon atoms, an amino group of the formula V $$-\underset{R^{15}}{\overset{\overset{R^{14}}{|}}{N}}\quad\quad\text{V}$$

wherein $R^{14}$ and $R^{15}$ are as above defined, or a group of the formula $R^{12}-SO_2-O-$, and the other of $R^8$ and $R^9$ is hydrogen, or $R^8$ and $R^9$ together form a oxo group or an oxime group of the formula IV $$=N\sim\sim\sim O-R^{13}\quad\quad\text{IV}$$

wherein $R^{13}$ is as above defined; the wavy line in formula IV has the meaning set forth above, and $R^{12}$ is a hydrocarbon of up to 18 carbon atoms, oxahydrocarbon of up to 18 carbon atoms, thiahydrocarbon of up to 18 carbon atoms or azahydrocarbon of up to 18 carbon atoms, each of which is either unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxyl, in combination with a pharmaceutically acceptable carrier.

15. A composition according to claim 14 wherein $R^3$ is of the formula $$R^A-O-CH_2-$$

$$R^B-CO-NH-CH_2-$$

$$R^B-CO-\underset{R^E}{\overset{|}{N}}-CH_2-$$

or $$\underset{R^F}{\overset{OC-N-CH_2-}{\diagdown|}}$$

in which $R^A$ is a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxyl and $R^B$ is hydrogen, a hydrocarbon of up to 18 carbon atoms or a hydrocarbon-oxy of up to 18 carbon atoms, said hydrocarbon and said hydrocarbon-oxy being unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxyl, $R^E$ is a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxy, and $R^F$ is a divalent hydrocarbon completing a 4- to 7-membered ring unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxyl.

16. A composition according to claim 14 wherein $R^A$ is is 2-substituted-ethyl or 3-substituted-propyl, in which the substituent is amino, N-alkylamino, N-N-dialkylamino, halogen, hydroxy, alkoxy, benozyloxy, alkanesulphonyloxy, trisilyloxy, alkoxycarbonyl, alkanoyloxy, phenoxy, or heterocyclyl.

17. A composition according to claim 14 wherein $R^1$ and $R^2$ together form a group of the formual IV:

 IV in which $R^{13}$ is hydrogen, a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxyl.

18. A composition according to claim 17 wherein $R^{13}$ is hydrogen or methyl.

19. A composition according to claim 14 wherein $R^4$ is hydroxy.

20. A composition according to claim 14 wherein $R^5$ is hydroxy.

21. A composition according to claim 14 wherein $R^7$ is methyl.

22. A composition according to claim 14 wherein $R^8$ is hydrogen and $R^9$ is hydroxy.

23. A pharmaceutical composition useful for treating bacterial infections in humans and animals which comprises an antibacterially effective amount of 11-O-(2-piperidin-1-yl)-ethoxymethyl)-erythromycin A 9-O-methoxime, in combination with a pharmaceutically acceptable carrier.

24. A method of treating bacterial infections in humans and animals which compries adminsitering to a human or animal in need thereof an antibacterially effective amount of a compound of the formula I

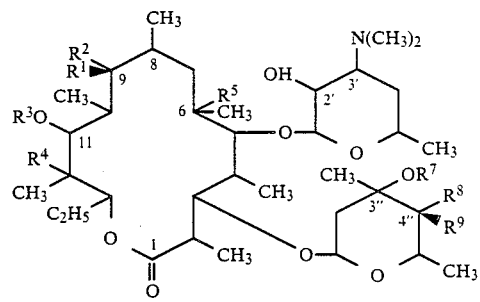

a pharmaceutically acceptable acid additon salt thereof or a pharmaceutically acceptable ester thereof wherein one of $R^1$ and $R^2$ is hydrogen and the other of $R^1$ and $R^2$ is an amino group of the formula V

 V wherein $R^{14}$ and $R^{15}$ are the same or different and each is hydrogen, a hydrocarbon of up to 18 carbon atoms, unsubstituted or substituted by heterocyclyl, amino, alkanoylamino of 1-6 atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxyl; or $R^1$ and $R^2$ together form an oxo group, an oxime group of the formula IV,

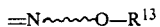 IV or an imino group, wherein $R^{13}$ is hydrogen, a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxyl; and wherein the wavy line in formula IV means the compounds can exist in the E- and Z-geometric isomeric forms about the C=N double bond at the 9-position; $R^5$ is hydroxy or alkoxy of up to 12 carbon atoms; or one of $R^1$ and $R^2$ is hydroxy, or amino, and the other of $R^1$ and $R^2$ together with $R^5$ forms an ether oxygen atom, —O—, $R^3$ is a group of the formula II:

 II in which Q is:

 IIIA

 IIIB

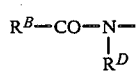 IIIC

-continued

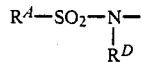     IIID wherein $R^A$ is a hydrocarbon of up to 18 carbon atoms unsubstituted or substituted by heterocyclyl, amino, alknoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxyl $R^B$ is hydrogen, a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxy or a hydrocarbon-oxy of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxyl; each of $R^C$ and $R^D$, are the same or different, and each is hydrogen, a hydrocarbon of up to 18 carbon atoms unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, caramoyl, amidino, guanidino, nitro, halo, carboxyl or a salt or ester thereof, acyl or acyloxyl, or any two of $R^A$, $R^B$, $R^C$ and $R^D$ are a divalent, organic group forming together with the intervening atoms of the molecule a 4- to 7-membered heterocyclic ring having up to 4 heteroatoms selected from the group consisting of oxygen, nitrogen and sulphur unsubstituted or substituted by up to 3 substituents selected from the group consisting of halo, alkyl of 1 to 6 carbon atoms, alkoxy of 1 to 6 carbon atoms, haloalkyl of 1 to 6 carbon atoms, hydroxy, amino, carboxyl or a salt or ester thereof, alkoxycarbonyl of 1 to 6 carbon atoms in the alkoxy moiety, alkoxycarbonylalkyl of 1 to 6 carbon atoms in each of the alkoxy and alkyl moieties, aryl and oxo;

$R^4$ is hydrogen or hydroxy;
$R^7$ is hydrogen or methyl;
one of $R^8$ and $R^9$ is hydrogen, hydroxy, alkoxy of 1 to 12 carbon atoms, alkanoyloxy of 1 to 12 carbon atoms, an amino group of the formula V

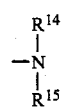     V wherein $R^{14}$ and $R^{15}$ are as above defined, or a group of the formula $R^{12}$—$SO_2$—O—, and the other of $R^8$ and $R^9$ is hydrogen, or $R^8$ and $R^9$ together form an oxo group or an oxime group of the formula IV

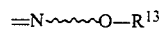     IV wherein $R^{13}$ is as above defined; the wavy line in formula IV has the meaning set forth above, and $R^{12}$ is a hydrocarbon of up to 18 carbon atoms, oxahydrocarbon of up to 18 carbon atoms, thiahydrocarbon of up to 18 carbon atoms or azahydrocarbon of up to 18 carbon atoms, each of which is either unsubstituted or substituted by heterocyclyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclylthio, arylthio, sulphamoyl, carbamoyl, amidino, guanidino, nitro, halo, carboxyl or a salt or ester thereof, acyl or acyloxyl, in combination with a pharmaceutically acceptable carrier.

25. A method according to claim 24 wherein $R^3$ is of the formula

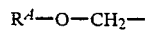

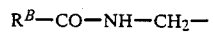

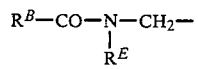

or

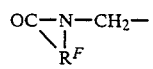

in which
$R^A$ is a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclythio, arylthio, sulphamoyl, carbamoyl, amidino, guanidino, nitro, halo, carboxyl or a salt or ester thereof, acyl or acyloxyl and $R^B$ is hydrogen, a hydrocarbon of up to 18 carbon atoms or a hydrocarbon-oxy of up to 18 carbon atoms, said hydrocarbon and said hydrocarbon-oxy being unsubstituted or substituted by heterocycyl, amino, alkanoylamino of 1-6 carbon atoms in each alkyl moiety, hydroxy, alkoxy of 1-6 carbon atoms, mercapto, alkylthio of 1-6 carbon atoms, in the alkyl moiety, heterocyclythio, arylthio, sulphamoyl, carbamoyl, amidino, guanidino, nitro, halo, carboxyl or a salt or ester thereof, acyl or acyloxyl, $R^E$ is a hydrocarbon of up to 18 carbon atoms, unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocyclythio, arylthio, sulphamoyl, carbamoyl, amidino, guanidino, nitro, halo, carboxyl or a salt or ester thereof,a cyl or acyloxyl, and $R^F$ is a divalent hydrocarbon completing a 4- to 7-membered ring unsubstituted or substituted by heterocycyl, amino, alkanoylamino of 1-6 carbon atoms in the alkyl moiety, mono-, di-, or tri-alkylamino of 1-6 carbon atoms in each alkyl moiety, hydroxy, alkoxy of 1-6 carbon atoms, mercapto, alkylthio of 1-6 carbon atoms in the alkyl moiety, heterocycylthio, arylthio, sulphamoyl, carbamoyl, amidino, guanidino, nitro, halo, carboxyl or a salt or ester thereof, acyl or acyloxyl.

26. A method according to claim 24 wherein $R^4$ is is 2-substituted-ethyl or 3-substituted-propyl, in which the substituent is amino, N-alkylamino, N,N-dialkylamino, halogen, hydroxy, alkoxy, benzoyloxy, alkanesulphonyloxy, trisilyloxy, alkoxycarbonyl, alkanoyloxy, phenoxy, or heterocycyl.

27. A method according to claim 24 wherein $R^{13}$ is hydrogen or methyl.

28. A method according to claim 24 wherein $R^4$ is hydroxy.

29. A method according to claim 24 wherein $R^5$ is hydroxy.

30. A method according to claim 24 wherein $R^7$ is methyl.

31. A method according to claim 24 wherein $R^8$ is hydrogen and $R^9$ is hydroxy.

32. A method according to claim 26 wherein $R^4$ is 2-subtituted-ethyl or 3-substituted-propyl in which the substituent is a nitrogen-containing heterocyclyl having from 4-7 ring atoms which is bonded through a ring nitrogen atom.

33. A compound according to claim 3 wherein $R^4$ is 2-substituted-ethyl or 3-substituted-propyl in which the substituent is triazolyl, piperidinyl or phthalimido bonded through a ring nitrogen atom.

34. A method of treating bacterial infections in humans and animals which comprises administering to a human or animal in need thereof an antibacterially effective amount of 11-O-(2-piperidin-1-yl)-ethoxymethyl)-erythromycin A 9-O-methoxime, in combination with a pharmaceutically acceptable carrier.

35. A pharmaceutical composition useful for treating bacterial infections in humans and animals which comprises an antibacterially effective amount of 11-O-[2-methylaminoethoxymethyl]-erythromycin A 9-O-methoxime, in combination with a pharmaceutically acceptable carrier.

36. A method of treating bacterial infections in humans and animals which comprises administering to a human or animal in need thereof an antibacterially effective amount of 11-O-[2di-methylaminoethoxymethyl]-erythromycin A 9-methoxime, in combination with a pharmaceutically acceptable carrier.

* * * * *